United States Patent [19]

Smith

[11] 4,131,738

[45] Dec. 26, 1978

[54] 6-HYDROXY-PGE$_1$ COMPOUNDS

[75] Inventor: Herman W. Smith, Kalamazoo Township, Kalamazoo County, Mich.

[73] Assignee: The Upjohn Company, Kalamazoo, Mich.

[21] Appl. No.: 812,794

[22] Filed: Jul. 5, 1977

[51] Int. Cl.$^2$ .......................................... C07L 177/00
[52] U.S. Cl. ................................... 560/121; 546/257; 546/258; 546/309; 546/298; 546/314; 546/226; 546/194; 546/261; 546/262; 260/234 B; 260/326.4; 260/346.22; 260/408; 260/410; 260/410.5; 260/410.9 R; 260/413; 260/463; 260/501.17; 542/429; 542/430; 542/431; 542/426
[58] Field of Search .................. 560/121; 260/514 D, 260/408, 410, 410.9 R, 410.5, 413

[56] References Cited

U.S. PATENT DOCUMENTS 4,045,449  8/1977  Bundy .............................. 260/340.2

Primary Examiner—Robert Gerstl
Attorney, Agent, or Firm—Robert A. Armitage

[57] ABSTRACT

This invention relates to certain structural analogs of the prostaglandins which have been unexpectedly discovered to be pharmacological analogs of prostacyclin (PGI$_2$), i.e., they exhibit the characteristic prostacyclin-type biological responses. These novel compounds are all 6-hydroxy-PGE-type compounds. They are useful for the pharmacological purposes for which prostacyclin is used, e.g., a antithromboti agents, smooth muscle stimulators, gastric antisecretory agents, antihypertensive agents, antiasthma agents, nasal decongestants, or regulators or fertility and procreation.

36 Claims, No Drawings

6-HYDROXY-PGE₁ COMPOUNDS

BACKGROUND OF THE INVENTION

This invention relates to novel structural analogs of prostaglandin E compounds which are pharmacological analogs of prostacyclin (PGI$_2$). In particular, the present invention relates to prostaglandin E-type compounds wherein the C-6 carbon atom is substituted by hydroxy.

Prostacyclin is an endogenously produced compound in mammalian species, being structurally and biosynthetically related to the prostaglandins (PG's). In particular, prostacyclin exhibits the following structural and atom numbering:

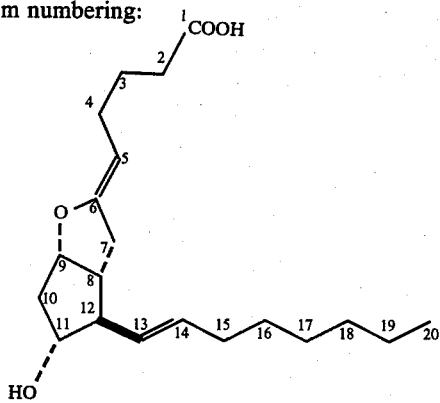

I

As is apparent from inspection of formula I, prostacyclin bears a structural relationship to other endogenously-produced fatty acids, e.g., PGF$_2\alpha$ and PGE$_2$, which respectively exhibit the following structure and atom numbering:

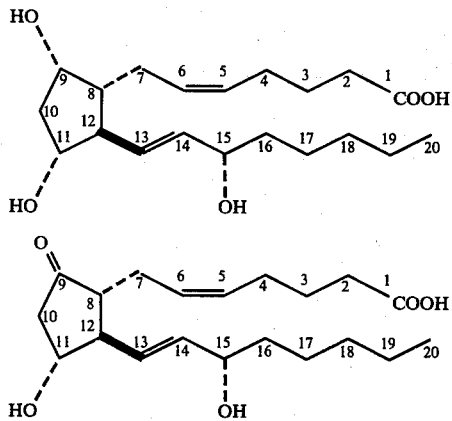

II

III

As is apparent by reference to formulas II and III, prostacyclin may be trivially named as a derivative of PGF-type compounds. Accordingly, prostacyclin is trivially named 9-deoxy-6,9α-epoxy-(5Z)-5,6-didehydro-PGF$_1$. For description of the geometric stereoisomerism employed above, see Blackwood et al., Journal of the American Chemical Society 90, 509 (1968). Further, for a description of prostacyclin and its structural identification, see Johnson et al, Prostaglandins 12, 915 (1976).

For convenience, both prostaglandin and prostacyclin analogs described herein will be referred to by the trivial, art-recognized system of nomenclature described by N. A. Nelson, Journal of Medicinal Chemistry, 17, 911 (1974) for the prostaglandins. Accordingly, all of the novel prostaglandin analogs will be named as derivatives of PGE$_1$ or PGE$_2$.

In formulas I, II, and III above, as well as in formulas hereinafter, broken line attachments to any ring indicate substituents in "alpha" (α) configuration, i.e., below the plane of such ring. Heavy solid line attachments to any ring indicate substituents in "beta" (β) configuration, i.e., above the plane of such ring. The use of wavy lines (∼) herein will represent attachment of substituents in either the alpha or beta configuration or attachment in a mixture of alpha and beta configurations.

The side-chain hydroxy at C-15 in the above formulas is in S or R configuration, as determined by the CahnIngold-Prelog sequence rules. See J. Chem. Ed. 41:16 (1964). See also Nature 212, 38 (1966) for discussion of the stereochemistry of the prostaglandins, which discussion applies to the novel prostaglandin analogs herein. Expressions such as C-6, C-15, and the like, refer to the carbon atom in the novel prostaglandin analog which is in the position corresponding to the position of the same number in PGF$_2\alpha$, PGE$_2$, or prostacyclin, as enumerated above.

Molecules of PGF$_2\alpha$ and PGE$_2$ as well as prostaglandin analogs each have several centers of asymmetry, and can exist in racemic (optically inactive) form and in either of the two enantiomeric (optically active) forms, i.e., the dextrorotatory and levorotatory forms. As drawn, the above formulas for PGF$_2\alpha$, PGE$_2$, and prostacyclin correspond to that endogenously produced in mammalian tissues. In particular, refer to the stereoconfiguration at C-8 (alpha), C-9 (alpha), C-11 (alpha), and C-12 (beta) of endogenously-produced PGF$_2\alpha$ and PGE$_2$. The mirror image of the above formulas for these prostaglandins represents the other enantiomer. The racemic forms of these prostaglandins contain equal numbers of both enantiomeric molecules, and one of the above formulas and its mirror image is needed to represent correctly the corresponding racemic prostaglandin.

For convenience hereinafter, use of the term prostaglandin ("PG") or prostacyclin ("PGI$_2$") will mean the optically active form of that prostaglandin or prostacyclin thereby referred to with the same absolute configuration as PGF$_2\alpha$, PGE$_2$, or prostacyclin obtained from mammalian tissues.

The term "prostaglandin-type" (PG-type) product, as used herein, refers to any monocyclic or bicyclic cyclopentane derivative herein which is useful for at least one of the same pharmacological purposes as the prostaglandins or prostacyclin.

The formulas as drawn herein, which depict a prostaglandin-type or prostacyclin-type product or an intermediate useful in their respective preparations, each represent the particular stereoisomer of the prostaglandin-type or prostacyclin-type product which is of the same relative stereochemical configuration as a corresponding prostaglandin or prostacyclin obtained from mammalian tissues, or the particular stereoisomer of the intermediate which is useful in preparing the above stereoisomer of the prostaglandin-type or prostacyclin-type products.

The term "prostaglandin analog", as used herein, represents that stereoisomer of a prostaglandin-type product which is of the same relative stereochemical configuration as a prostaglandin obtained from mammalian tissues or a mixture comprising that stereoisomer and the enantiomer thereof. In particular, where a formula is used to depict a prostaglandin-type product herein, the term "prostaglandin analog" refers to the compound of that formula or a mixture comprising that compound and the enantiomer thereof.

The use of 6-hydroxyprostanol derivatives in the preparation of 4,4,5,5-tetradehydro-PG-type compounds is described in U.S. Pat. No. 4,013,695. See especially Chart C therein at columns 27–30 and the text related thereto.

SUMMARY OF THE INVENTION

The present invention particularly comprises: a prostaglandin analog of the formula

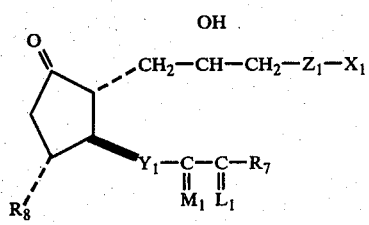

wherein $Z_1$ is
(1) —$(CH_2)_g$—$CH_2$—$CH_2$—,
(2) —$(CH_2)_g$—$CH_2$—$CF_2$—, or
(3) trans—$(CH_2)_g$—CH=CH—,
wherein g is the integer one, 2, or 3;
wherein $R_8$ is hydrogen, hydroxy, or hydroxymethyl;
wherein $Y_1$ is
(1) trans—CH=CH—,
(2) cis—CH=CH—,
(3) —$CH_2CH_2$—,
(4) trans—CH=C(Hal)—, or
(5) —C≡C—
wherein Hal is chloro or bromo; wherein $M_1$ is

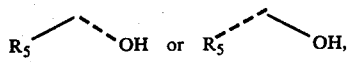

wherein $R_5$ is hydrogen or alkyl with one to 4 carbon atoms, inclusive,
wherein $L_1$ is

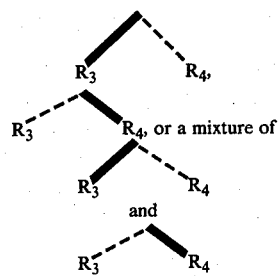

wherein $R_3$ and $R_4$ are hydrogen, methyl, or fluoro, being the same or different, with the proviso that one of $R_3$ and $R_4$ is fluoro only when the other is hydrogen or fluoro;
wherein $X_1$ is
(1) —$COOR_1$ wherein $R_1$ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted with one, two, or three chloro or alkyl of one to 3 carbon atoms; phenyl substituted in the para position by

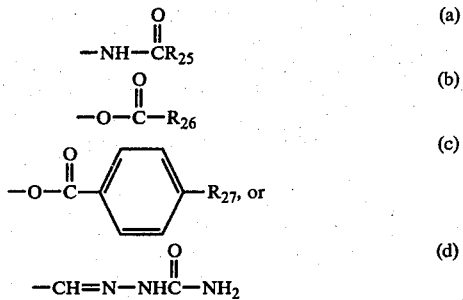

wherein $R_{25}$ is methyl, phenyl, acetamidophenyl, benzamidophenyl, or —$NH_2$; $R_{26}$ is methyl, phenyl, —$NH_2$, or methoxy; and $R_{27}$ is hydrogen or acetamido, inclusive, or a pharmacologically acceptable cation;
(2) —$CH_2OH$;
(3) —$CH_2NL_2L_3$, wherein $L_2$ and $L_3$ are hydrogen or alkyl of one to 4 carbon atoms, inclusive or being the same or different;
(4) —$COL_4$, wherein $L_4$ is
(a) amino of the formula —$NR_{21}R_{22}$, wherein $R_{21}$ and $R_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive; hydroxy of one to 3 carbon atoms, inclusive, carboxy, alkoxycarbonyl of one to 4 carbon atoms, inclusive; or nitro; carboxyalkyl of one to four carbon atoms, inclusive; carbamoylalkyl of one to four carbon atoms, inclusive; cyanoalkyl of one to four carbon atoms, inclusive; acetylalkyl of one to four carbon atoms, inclusive; benzoylalkyl of one to four carbon atoms, inclusive; benzoylalkyl substituted by one, 2, or 3 chloro, alkyl of one to 3 carbon atoms inclusive; hydroxy, alkoxy of one to 3 carbon atoms, inclusive; carboxy, alkoxycarbonyl of one to 4 carbon atoms, inclusive; or nitro; pyridyl; pyridyl substituted by one, 2, or 3 chloro, alkyl of one to 3 carbon atoms, inclusive; or alkoxy of one to 3 carbon atoms, inclusive; pyridylalkyl of one to 4 carbon atoms, inclusive; pyridylalkyl of one to 4 carbon atoms, inclusive; pyridylalkyl substituted by one, 2, or 3 chloro, alkyl of one to 3 carbon atoms, inclusive; hydroxy, alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms; with the further proviso that not more than one of $R_{21}$ and $R_{22}$ is other than hydrogen or alkyl;
(b) cycloamino selected from the group consisting of

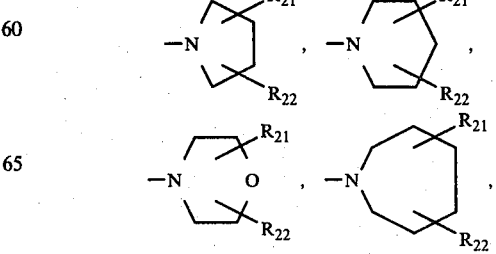

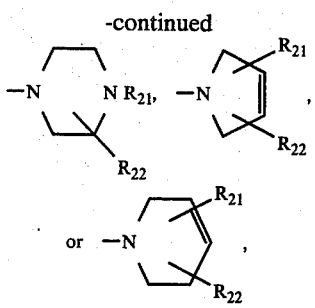

wherein $R_{21}$ and $R_{22}$ are as defined above;

(c) carbonylamino of the formula $-NR_{23}COR_{21}$, wherein $R_{23}$ is hydrogen or alkyl of one to 4 carbon atoms and $R_{21}$ is as defined above;

(d) sulfonylamino of the formula $-NR_{23}SO_2R_{21}$, wherein $R_{21}$ and $R_{22}$ are as defined above; or (e) hydrazino of the formula $-NR_{22}R_{24}$, wherein $R_{24}$ is amino of the formula $-NR_{21}R_{22}$, as defined above, or cycloamino, as defined above; or (5) tetrazolyl; and wherein $R_7$ is

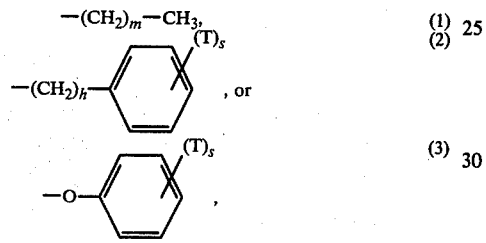

wherein m is the integer one to 5, inclusive; h is the integer zero to 3, inclusive; s is the integer zero, one, 2, or 3; and T is chloro, fluoro, trifluoromethyl, alkyl of one to 3 carbon atoms, inclusive; or alkoxy of one to 3 carbon atoms, inclusive; with the proviso that not more than two T's are other than alkyl; and the pharmacologically acceptable acid addition salts thereof when $X_1$ is $-CH_2NL_2L_3$ and $L_2$ and $L_3$ are hydrogen or alkyl.

For the novel compounds herein where $Z_1$ is $-(CH_2)_g-CH_2-CF_2-$, such compounds are referred to herein as 2,2-difluoro-PGE$_1$-type compounds. Further, compounds herein wherein $Z_1$ is trans—$(CH_2)_g-CH=CH-$ are named as trans—2,3-didehydro-PGE$_1$-type compounds.

When g is 2 or 3, the compounds described herein are additionally named as 2a-homo-PG-type or 2a,2b-dihomo-PGE$_1$-type compounds, respectively. In this event the additional methylene or ethylene group is considered for the purposes of nomenclature as though it were inserted between the carbon atoms C-2 and C-3. Further, such additional carbon atoms are denoted as C-2a and C-2b, counting from the C-2 to the C-3 carbon atoms, respectively.

The novel prostaglandin analogs herein wherein $R_8$ is hydrogen or hydroxymethyl are respectively referred to as 11-deoxy-PGE$_1$-type or 11-deoxy-11-hydroxymethyl-PGE$_1$-type compounds. Additionally, when $Y_1$ is cis—$CH=CH-$, $-CH_2CH_2-$, trans—$CH=C(Hal)-$, or $-C\equiv C-$, the novel compounds thereby referred to are named as 13-cis-PGE$_1$-type, 13,14-dihydro-PGE$_1$-type, 14-halo-PGE$_1$-type, or 13,14-didehydro-PGE$_1$-type compounds.

Compounds herein wherein $R_5$ is alkyl are referred to as 15-alkyl-PGE$_1$-type compounds.

With the exception of the 13-cis-PG-type compounds described above, all the above compounds exhibiting an hydroxy in the beta configuration at C-15 are additionally referred to as 15-epi-PGE$_1$-type compounds. For the 13-cis-PG-type compounds herein, only compounds exhibiting the hydroxy in the alpha configuration at C-15 are referred to as 15-epi-PGE$_1$-type compounds. The rationale for this system of nomenclature with respect to the natural and epimeric configurations at C-15 is described in U.S. Pat. No. 4,016,184, issued Apr. 5, 1977.

When $R_7$ is $-(CH_2)_m-CH_3$, wherein m is as defined above, the novel compounds herein are named as 19,20-dinor-PGE$_1$-type, 20-nor-PGE$_1$-type, 20-methyl-PGE$_1$-type or 20-ethyl-PGE$_1$-type compounds when m is one, 2, 4, or 5, respectively.

When $R_7$ is

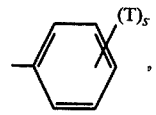

wherein l and s are as defined above, and neither $R_3$ nor $R_4$ is methyl, the novel compounds herein are named as 16-phenyl-17,18,19,20-tetranor-PGE$_1$-type compounds, when s is zero. When s is one, 2, or 3, the corresponding compounds are named as 16-(substituted phenyl)-17,18,19,20-tetranor-PGE$_1$-type compounds. When one and only one of $R_3$ and $R_4$ is methyl or both $R_3$ and $R_4$ are methyl, then the corresponding compounds wherein $R_7$ is as defined in this paragraph are named as 16-phenyl- or 16-(substituted phenyl-18,19,20-trinor-PGE$_1$-type; or 16-methyl-16-phenyl- or 16-methyl- or 16-(substituted phenyl)-18,19,20-trinor-PGE$_1$-type compounds, respectively.

When $T_7$ is

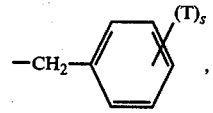

wherein R and s are as defined above, the novel compounds herein are named as 17-phenyl-18,19,20-trinor-PGE$_1$-type compounds, when s is 0. When s is one, 2, or 3, the corresponding compounds are named as 17-(substituted phenyl)-18,19,20-trinor-PGE$_1$-type compounds.

When $R_7$ is

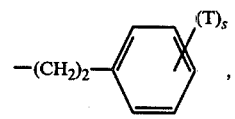

wherein T and s are as defined above, the novel compounds herein are named as 18-phenyl-19,20-dinor-PGE$_1$-type compounds, when s is 0. When s is one, 2, or 3, the corresponding compounds are named as 18-(substituted phenyl)-19,20-dinor-PGE$_1$-type compounds.

When $R_7$ is

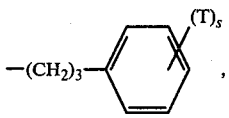

wherein T and s are as defined above, the novel compounds herein are named as 19-phenyl-20-nor-PGE$_1$-type compounds, when s is 0. When s is one, 2, or 3, the corresponding compounds are named as 19-(substituted phenyl)-20-nor-PGE$_1$-type compounds.

When R$_7$ is

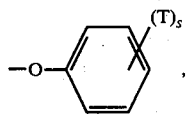

wherein T and s are as defined above, and neither R$_3$ nor R$_3$ is methyl, the novel compounds herein are named as 16-phenoxy-17,18,19,20-tetranor-PGE$_1$-type compounds, when s is zero. When s is one, 2, or 3, the corresponding compounds are named as 16-(substituted phenoxy)-17,18,19,20-tetranor-PGE$_1$-type compounds. When one and only one of R$_3$ and R$_4$ is methyl or both R$_3$ and R$_4$ are methyl, then the corresponding compounds wherein R$_7$ is as defined in this paragraph are named as 16-phenoxy- or 16-(substituted phenoxy)-18,19,20-trinor-PGE$_1$-type compounds or 16-methyl-16-phenoxy- or 16-substituted phenoxy)-18,19,20-trinor-PGE$_1$-type compounds, respectively.

When at least one of R$_3$ and R$_4$ is not hydrogen then (except for the 16-phenoxy or 16-phenyl compounds discussed above), there are thusly described the 16-methyl-PG-type (one and only one of R$_3$ and R$_4$ is methyl), 16,16-dimethyl-PGE$_1$-type (R$_3$ and R$_4$ are both methyl), 16-fluoro-PGE$_1$-type (one and only one of R$_3$ and R$_4$ is fluoro), and 16,16-difluoro-PGE$_1$-type (R$_3$ and R$_4$ are both fluoro) compounds. For those compounds wherein R$_3$ and R$_4$ are different, the prostaglandin analogs so represented contain an asymmetric carbon atoms at C-16. Accordingly, two epimeric configurations are possible: "(16S)" and "(16R)". Further, there is described by this invention the C-16 epimeric mixture: "(16RS)".

When X$_1$ is —CH$_2$OH or —CH$_2$L$_2$L$_3$, the novel compounds herein are named as 2-decarboxy-2-hydroxymethyl-PGE$_1$-type or 2-decarboxy-2-aminomethyl- or 2-(substituted amino)methyl-PGE$_1$-type compounds. When X$_1$ is tetrazolyl, the novel compounds herein are named as 2-decarboxy-2-tetrazolyl-PGE$_1$-type compounds.

When X$_1$ is -COL$_4$ the novel compounds herein are named as PG-type, amides. Further when X$_1$ is —COOR, the novel compounds herein are named as PG-type, esters and PG-type, salts when R$_1$ is not hydrogen.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopen- tyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-trimethylphenyl, (o-, m-, p-)fluorophenyl, 1-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3-, or 4-)chloro-2-fluorophenyl, (o-, m-, or p-)trifluoromethylphenyl, (o-, m-, or p-)methoxyphenyl, (o-, m-, or p-)ethoxyphenyl, (4- or 5-)chloro-2-methoxyphenyl, and 2,4-dichloro(5- or 6-)methylphenyl.

Examples of phenyl esters substituted in the para position (i.e., X$_1$ is -COOR$_1$, R$_1$ is p-substituted phenyl) include p-acetamidophenyl ester, p-benzamidophenyl ester, p-(p-acetamidobenzamideo)phenyl ester, p-(p-benzamidobenzamido)phenyl ester, p-amidocarbonylamidophenyl ester, p-acetylphenyl ester, p-benzyl-phenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel prostacyclin amides herein (i.e., X$_1$ is COL$_4$) include the following:

(1) Amides within the scope of alkylamino groups of the formula -NR$_{21}$R$_{22}$ are methylamide, ethylamide, n-propylamide, n-butylamide, n-pentylamide, n-hexylamide, n-heptylamide, n-octylamide, n-nonylamide, n-decylamide, n-undecylamide and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-ethyl-N-cyclohexylamide, dicyclopentylamide, and dicyclohexylamide. Amides within the scope of aralkylamino are benzylamide, 2-phenylethylamide, 2-phenylethylamide, N-methyl-N-benzylamide, and dibenzylamide. Amides within the scope of substituted phenylamino are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methylanilide, p-ethylanilide, t-butylanilide, p-carbocyanilide, p-methoxycarbonylanilide, o-carboxyanilide and o-hydroxyanilide. Amides within the scope of carboxyalkylamino are carboxymethylamide, carboxyethylamide, carboxypropylamide, and carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxybenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butyl-benzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pryidylamide, and γ-pryidylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamino are 4-methyl-α-pyridylmethylamide, 4-methyl-β-pyridylmethylamide, 4-chloropyridylmethylamide, 4-chloro-β-pyridylmethylamide, 4-methyl-α-pyridylethylamide, 4-methyl-β-pyridylethylamide, 4-chloropyridylethylamide, 4-chloro-β-pyridylethylamide, 4-methyl-α-pyridylpropylamide, 4-methyl-β-pyridylpropylamide, 4-chloro-pyridylpropylamide, 4-chloro-β-pyridylpropylamide, 4-methyl-β-pyridylbutylamide, 4-methyl-α-pryidylbutylamide, 4-chloropyridylbutylamide, 4-chloro-β-pyridylbutylamide, 4-methyl-β-pyridylbutylamide. Amides within the scope of hydroxyalkylamino are hydroxymethylamide, α-hydroxyethylamide, β-hydroxyethylamide, α-hydroxypropylamide, β-hydroxypropylamide, γ-hydroxypropylamide, 1-(hydroxymethyl)ethylamide, 1-(hydroxymethyl)propylamide, (2-hydroxymethyl)propylamide, and α,α-dimethyl-β-hydroxyethylamide. Amides within the scope of dihydroxyalkylamino are dihydroxymethylamide, α,α-dihydroxyethylamide, α,β-dihydroxyethylamide, β,β-dihydroxyethylamide, α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)2-hydroxyethylamide, 1-(hydroxymethyl)-1-hydroxyethylamide, α,α-dihydroxybutylamide, α,β-dihydroxybutylamide, α,γ-dihydroxybutylamide, α-γ-dihydroxybutylamide, β,β-dihydroxybutylamide, β,γ-dihydroxybutylamide, β,δ-dihydroxybutylamide, γ,γ-dihydroxybutylamide, γ,δ-dihydroxybutylamide, δ,δ-dihydroxybutylamide, and 1,1-bis(hydroxymethyl)ethylamide. Amides within the scope of trihydroxyalkylamino are tris(hydroxymethyl)methylamide andr 1,3-dihydroxy-2-hydroxymethyl-propylamide.

(2) Amides within the scope of the cycloamino groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamino of the formula -NR$_{23}$COR$_{21}$ are methylcarbonylamide, ethylcarbonylamide, phenylcarbonylamide, and benzylcarbonylamide. Amides within the scope of sulfonylamino of the formula -NR$_{23}$SO$_2$R$_{21}$ are methylsulfonylamide, ethylsulfonylamide, phenylsulfonylamide, p-tolylsulfonylamide, benzylsulfonylamide.

(4) Hydrazides within the scope of the above hydrazino groups are hydrazine, N-aminopiperidine, benzoylhydrazine, phenylhydrazine, N-aminomorpholine, 2-hydroxyethylhydrazine, methylhydrazine, 2,2,2-hydroxyethylhydrazine and p-carboxyphenylhydrazine.

The term "pharmacologically acceptable acid addition salt" refers to those known acid addition salts of the 2-decarboxy-2-aminomethyl-PGE$_1$ compounds which are relatively non-toxic and readily acceptable to the host animal. Especially preferred are those acid addition salts which facilitate pharmaceutical formulation (e.g., more readily crystalline, etc.) or are readily and easily available for use. In particular, examples of acids from which such salts may be prepared are hydrochloric acid, hydrobromic acid, sulphuric acid, phosphoric acid, and other acids such as tartaric acid, fumaric acid, maleic acid, methanesulfonic acid, and p-toluene sulfonic acid.

The term "pharmacologically acceptable cation" refers to those pharmacologically acceptable salts of the prostaglandin-type carboxylic acids (X$_1$ is -COOH) described above which are conventionally employed with prostaglandins. In particular, such pharmacologically acceptable salts include pharmacologically acceptable metal cations, amine cations, and quarternary amonium cations. Additionally, basic amino acids such as arginine and lysine are employed. Further, certain amine cations such as THAM [tris(hydroxymethyl)amino methyl] and adamanamine are especially useful for the present purposes. Additionally, United States Pat. No. 3,016,184, issued Apr. 5, 1977 (particularly column 29), describes salts which are likewise preferred for the present purposes.

The novel prostaglandin analogs disclosed herein produce a multiplicity of prostacyclin-like biological responses, rendering these compounds useful for a variety of pharmacological purposes. In particular, the biological responses include platelet aggregation inhibition, smooth muscle stimulation, blood pressure lowering, gastric secretion reduction, NOSAC (nonsteroidal antiinflammatory compound)-induced lesion inhibition, bronchodilation, nasal decongestion, peripheral vascular circulatory improvement, renal blood flow alteration, dermatosis reversal, inflammation reduction, and intraocular pressure reduction.

Accordingly, the novel prostaglandin analogs of the present invention are used as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys), as follows:

(a) Platelet Aggregation Inhibition. The novel prostaglandin analogs herein are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, and to treat conditons such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The preferred dosage form for these compounds is oral, although other non-parenteral routes (e.g., buccal, rectal, sublingual) are likewise employed in preference to parenteral routes. Oral dosage forms are conventionally formulated (tablets, capsules, et cetera) and administered 2 to 4 times daily. Doses in the range of about 0.05 to 100 mg./kg. of body weight per day are effective.

The addition of these compounds to whole blood provides in vitro applications such as, storage of whole blood to be used in heart-lung machines. Additionally whole blood containing these compounds can be circulated through organs, e.g. heart and kidneys, which have been removed from a donor prior to transplant. They are also useful in treating thrombocytopenia, chemotherapy, and radiation therapy. In vitro applications utilize a dose of 0.001-1.0 µg/ml of whole blood.

(b) Smooth Muscle Stimulation. The novel prostaglandin analogs herein are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 µg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight and condition of the patient or animal.

(c) Blood Pressure Lowering.

The novel prostaglandin analogs herein are useful as hypotensive agents to reduce blood pressure in mammals, including man. For this purpose, the compounds are administered by intravenous infusion at the rate about 0.01 to about 50 µg. per kg. of body weight per minute or in single or multiple doses of about 25 to 500 µg. per kg. of body weight total per day.

As for the antithrombic application described above, these compounds are most preferably administered orally or by other convenient non-parenteral dosage form. In determining the appropriate oral dosage and frequency of administration titration of dose in conjunction other antihypertensive drugs being concomitantly administered is required. When used as the sole antihypertensive agent, determining the minimum effective dose required for adequate control of blood pressure is undertaken by initiating therapy at or near the threshold dose of patient or animal response. Thereafter upward adjustment of the dosage, until full control is achieved or undesired side effects are observed, is undertaken. Accordingly threshold dosages of 0.01 to 1.0 mg./kg. of body weight are employed.

(d) Gastric Secretion Reduction.

The novel prostaglandin analogs herein are also useful in mammals, including man and certain useful animals, e.g., dogs and pigs, to reduce and control gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg. to about 20 µg. per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

Preferably, however, the novel prostaglandin analogs are administered orally or by other nonparenteral routes. As employed orally, one to 6 administrations daily in a dosage range of about 1.0 to 100 mg./kg. of body weight per day is employed. Once healing of the ulcers has been accomplished the maintenance dosage required to prevent recurrence is adjusted downward so long as the patient or animal remains asymptomatic.

(e) NOSAC-Induced Lesion Inhibition.

The novel prostaglandin analogs herein are also useful in reducing the undesirable gastrointestinal effects resulting from systemic administration of anti-inflammatory prostaglandin synthetase inhibitors, and are used for that purpose by concomitant administration of the prostaglandin derivative and the anti-inflammatory prostaglandin synthetase inhibitor. See Partridge, et al., U.S. Pat. No. 3,781,429, for a disclosure that the ulcerogenic effect induced by certain non-steroidal anti-inflammatory agents in rats is inhibited by concomitant oral administration of certain prostaglandins. Accordingly the novel prostaglandin analogs herein are useful, for example, in reducing the undesirable gastrointestinal effects resulting from systemic administration of indomethacin, phenylbutazone, and aspirin. These are substances specifically mentioned in Partridge, et al. as nonsteroidal, anti-inflammatory agents. These are also known to be prostaglandin synthetase inhibitors.

The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration.

The prostaglandin derivative is administered along with the anti-inflammatory prostaglandin synthetase inhibitor either by the same route of administration or by a different route. For example, if the anti-inflammatory substance is being administered orally, the novel prostacyclin analog is also administered orally, or, alternatively, is administered rectally in the form of a suppository or, in the case of women, vaginally in the form of a suppository or a vaginal device for slow release, for example, as described in U.S. Pat. No. 3,545,439. Alternatively, if the anti-inflammatory substance is being administered rectally, the novel prostaglandin analog is also administered rectally. Further, the novel prostaglandin analog can be conveniently administered orally or, in the case of women, vaginally. It is especially convenient when the administration route is to be the same for both anti-inflammatory substance and novel prostaglandin analog, to combine both into a single dosage form.

The dosage regimen for the novel prostaglandin analog in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular prostaglandin analog to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the novel prostaglandin analog to reduce and then substantially to eliminate those undesirable effects.

(f) Bronchodilatation.

The novel prostaglandin analogs herein are also useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandin analogs can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

These compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, sodium bissulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691, for example.

(g) Nasal Decongestion.

The novel prostaglandin analogs herein are useful in mammals, including man, as nasal decongestants and are used for this purpose in a dose range of about 10 $\mu$g. to about 10 mg. per ml. of a pharmacologically suitable liquid vehicle or as an aerosol spray, both for topical application.

(h) Peripheral Vascular Circulatory Improvement.

The novel prostaglandin analogs herein are useful in treating peripheral vascular disease in humans. The term peripheral vascular disease as used herein means disease of any of the blood vessels outside of the heart and disease of the lymph vessels, for example, frostbite, ischemic cerebrovascular disease, artheriovenous fistulas, ischemic leg ulcers, phlebitis, venous insufficiency, gangrene, hepatorenal syndrome, ductus arteriosus, non-obstructuve mesenteric ischemia, arteritis lymphangitis and the like. These examples are included to be illustrative and should not be construed as limiting the term peripheral vascular disease. For these conditions the compounds of this invention are administered orally or parenterally via injection or infusion directly into a vein or artery, intravenous or intraarterial injections being preferred. The dosages of these compounds are in the range of 0.01–1.0 $\mu$g./kg. of body weight administered by infusions at an hourly rate or by injection on a daily basis, i.e. 1–4 times a day, the exact dose depending on the age, weight, and condition of the patient and on the frequency and route of administration. Corresponding oral doses are in the range 0.05–50 mg. every 2 hrs. during up to a maximum of 6 administrations daily. Treatment is continued for one to five days, although three days is ordinarily sufficient to assure long-lasting therapeutic action. In the event that systemic or side effects are observed the dosage is lowered below the threshold at which such systemic or side effects are observed.

(i) Renal Blood Flow Alteration.

The novel prostaglandin analogs herein increase the flow of blood in the mammalian kidney, thereby increasing volume and electrolyte content of the urine. For that reason, these compounds are useful in managing cases of renal dysfunction, especially those involving blockage of the renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

(j) Dermatosis Reversal.

The novel prostaglandin analogs herein are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness or noticeably, but incompletely cleared, or completely cleared.

For these purposes, these compounds are applied topically as compositions including a suitable pharmaceutical carrier, for example, as an ointment, lotion, paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or peri-lesionally, or subcutaneously, using appropriate sterial saline compositions.

(k) Inflammation Reduction.

The novel prostaglandin analogs herein are useful as antiinflammatory agents for inhibiting chronic inflammation in mammals including the swelling and other unpleasant effects thereof using methods of treatment and dosages generally described for the therapeutic agents in U.S. Pat. No. 3,885,041, which patent is incorporated herein by reference.

(l) Reduction of Intraocular Pressure.

The novel prostaglandin analogs herein are finally useful in man for the reduction of intraocular pressure in those disease states where abnormally elevated pressure in the eye is a threat to the sight of the patient (i.e., glaucoma). While many routes of administration are successfully employed for this purpose, direct application of a sterile ophthalmic solution (e.g., in the form of drops) is the preferred route for convenience and minimization of systemic effects. While ultimate dosage is readily determined by patient response in the exhibition of significantly lower intraocular pressure and the absence of localized side effects, such as irritation of eye tissues, initial dosage levels of about 0.05 mg. to 50 mg. per several drops of sterile ophthalmic solution, repeated 2 to 4 times per day, are employed. For optimizing the absorption of drug when administered in the form of drops, the 2-decarboxy-2-aminomethyl-PGE$_1$ analogs herein are employed.

The novel prostaglandin analogs herein are thus surprisingly and unexpectedly useful for a wide variety of pharmacological purposes, rendering these compounds pharmacological analogs of prostacyclin. Moreover, the prostaglandin analogs herein exhibit a more prolonged chemical stability, as compared to prostacyclin, facilitating their formulation and use as pharmacological agents. Finally, these novel prostaglandin analogs exhibit improved utility as compared to prostacyclin when employed, as described above, as antithrombotic, antiasthma, or antiinflammatory agents. This improved utility is evidenced in that the novel prostacyclin analogs of this invention exhibit increased potency or selectivity of action, thus exhibiting fewer undesirable side effects when administered for one of these preferred pharmacological uses.

Within the scope of the novel prostaglandin analogs described above, certain compounds are preferred in that they exhibit increased potency, selectivity of action, or otherwise represent especially convenient and useful agents, especially for the preferred uses described above.

With respect to $Z_1$, preferred compounds are those wherein $Z_1$ is $-(CH_2)_g-CH_2-CH_2-$. Further, g is preferably the integer one or 3, most preferably being one. With respect to the $Y_1$ moiety, preferred compounds are those wherein $Y_1$ is trans—CH=CH—, —$CH_2CH_2$— or —C≡C—, the most especially preferred compounds being those wherein $Y_1$ is trans—CH=CH—. With respect to the $M_1$ moiety, preferred compounds are those wherein $M_1$ is

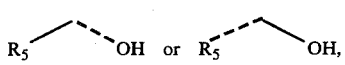

$R_5$ is preferably hydrogen or methyl.

With respect to the $L_1$ moiety, those compounds wherein $R_3$ and $R_4$ are the same are preferred. Further preferred are those compounds herein wherein at least $R_3$, $R_4$, and $R_5$ is hydrogen. In the event $Y_1$ is cis—CH=CH— or —C≡C—, compounds wherein $R_3$, $R_4$, and $R_5$ are all hydrogen are preferred.

With respect to the integers m, h, and s, it is preferred that m be the integer 3, h be the integer zero or 1, and s be the integer zero or one. Further, T is preferably chloro, fluoro, or trifluoromethyl.

Further preferred are the carboxylic acids or derivatives, i.e., esters, especially the p-substituted phenyl esters, and amides. With respect to the novel amides herein, preferred compounds are those wherein $R_{21}$ and $R_{22}$ are preferably hydrogen or alkyl of one to 8 carbon atoms, inclusive, being the same or different, preferably with the total number of carbon atoms in $R_{21}$ and $R_{22}$ being less than or equal to 8. More especially preferred are those amides wherein $R_{21}$ and $R_{22}$ are hydrogen or alkyl of one to 4 carbon atoms, inclusive, being the same or different, with the total number of carbon atoms in $R_{21}$ and $R_{22}$ being less than or equal to 4. Further, $R_{23}$ is preferably hydrogen.

CHART A

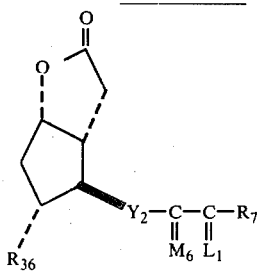

XXI

-continued

CHART A

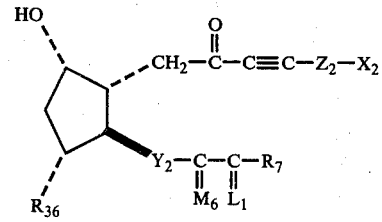

XXII

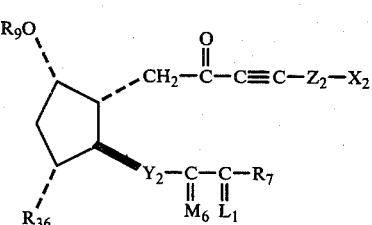

XXIII

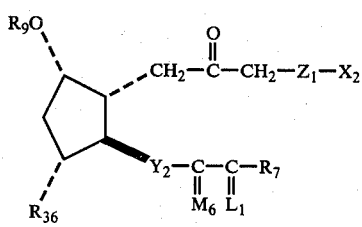

XXIV

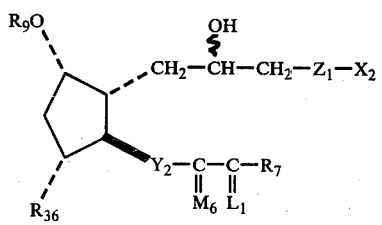

XXV

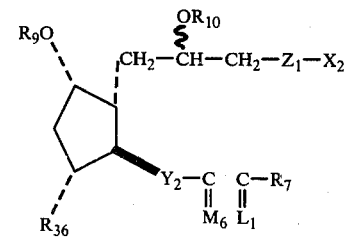

XXVI

-continued
CHART A
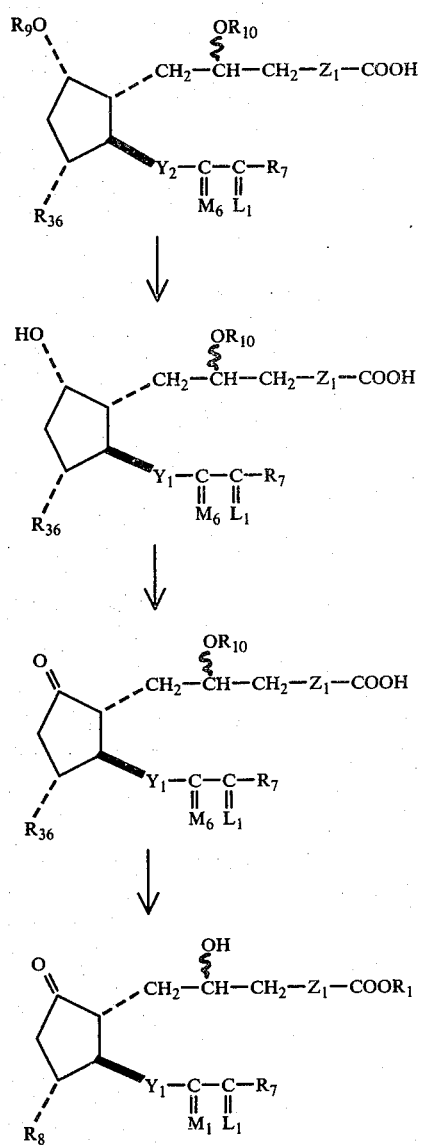
CHART B
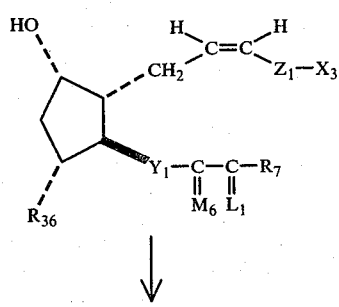
-continued
CHART B
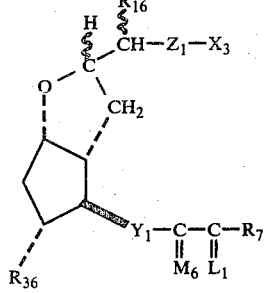
XXXII
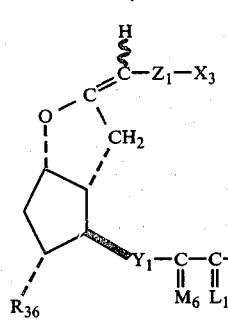
XXXIII
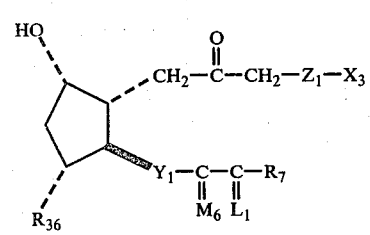
XXXIV
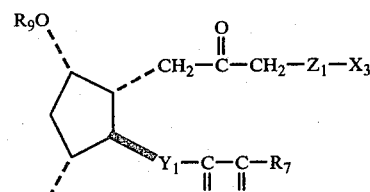
XXXV
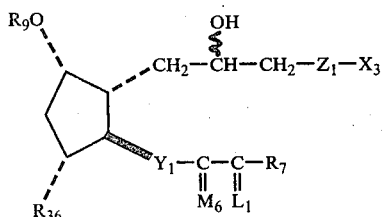
XXXVI -continued
CHART B
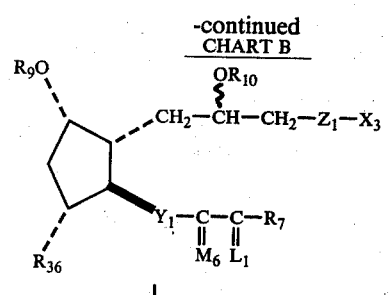 XXXVII
↓
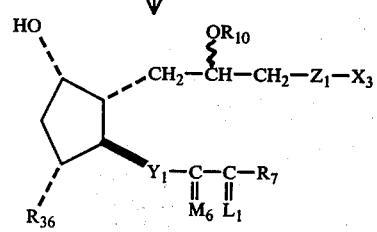 XXXVIII
↓
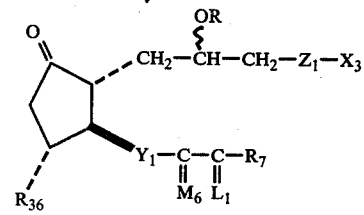 XXXIX
↓
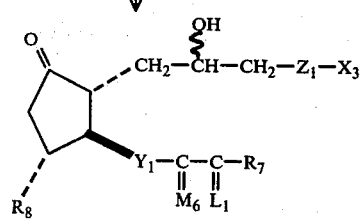 XL
CHART C
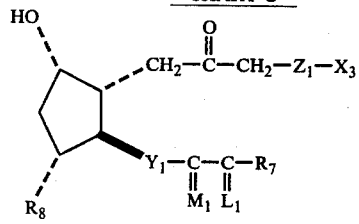 XLI
↓
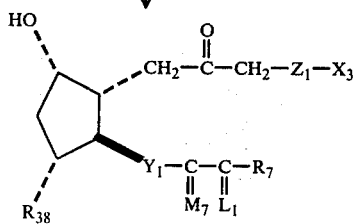 XLII
↓
-continued
CHART C
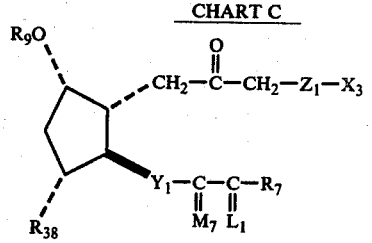 XLIII
↓
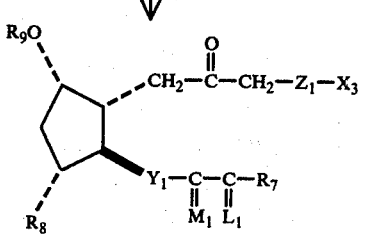 XLIV
↓
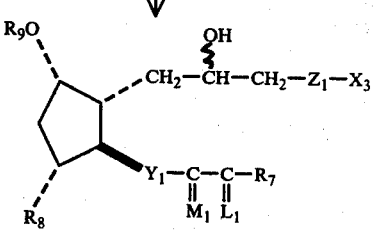 XLV
↓
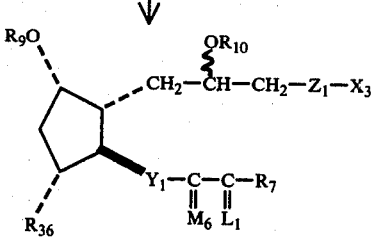 XLVI
↓
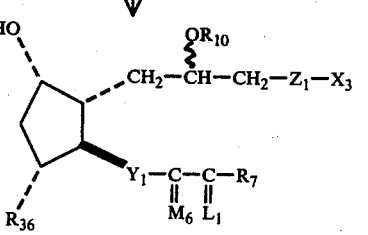 XLVII
↓
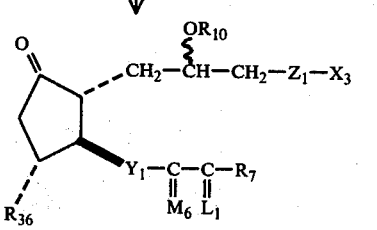 XLVIII
↓

-continued
CHART C

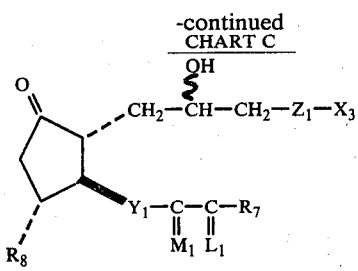

XLIX

The charts hereinafter describe methods by which the preparation of the novel prostaglandin analogs of the present invention is accomplished. With reference to these charts, $R_7$, $R_8$, $L_1$, $M_1$, $Y_1$, and $Z_1$ are as defined above. $Y_2$ corresponds to $Y_1$, except $Y_2$ is trans-CH=C(Hal)— in place of the -C≡C- moiety of $Y_1$. $R_9$ is a basesaponified acyl protecting group, being particularly acetyl, benzoyl, or p-phenylbenzoyl. Those acyl protecting groups contemplated by the present invention are those described by U.S. Pat. No. 4,061,184, which further provides processes applicable to the introduction and saponification of such groups as used by the present invention.

$R_{10}$ is a readily acid hydrolyzable blocking group, being particularly an acetal-type blocking group such as tetrahydropyranyl. Those readily acid hydrolyzable blocking groups contemplated by the present invention are particularly those described in United States Pat. No. 4,016,184, which further describes the methods for their introduction and hydrolysis which are applicable to their use in the present invention.

$R_{16}$ is bromo or iodo.

$R_{36}$ is $-OR_{10}$, $-CH_2OR_{10}$, or hydrogen, wherein $R_{10}$ is as defined above. $R_{38}$ is $-OSi(G_1)_3$, $-CH_2OSi(G_1)_3$, or hydrogen, wherein the $-Si(G_1)_3$ moiety represents a silyl replacing group for the free hydroxy. Preferably, this moiety is t-butyldimethylsilyl, although other silyl groups, particularly those described in U.S. Pat. No. 4,016,184, are employed. This patent further describes the method by which such groups are introduced and subsequently hydrolyzed under mild acid conditions. Particularly, see Corey, et al. JACS 94:6190 (1972), describing a method for selective hydrolysis of such silyl groups employing tetra-n-butylammonium fluoride in tetrahydrofuran. $M_6$ corresponds to $M_1$, except that the free hydroxyl moieties of $M_1$ are transformed to $R_{10}$ ethers. $M_7$ likewise corresponds to $M_1$, except that the secondary hydroxyls are transformed to corresponding silyl ethers.

$Z_2$ is $-(CH_2)_g-CH_2-$, $-(CH_2)_g-CF_2$, or trans-$(CH_2)_g-CH=CH-$, wherein g is as defined above.

$X_2$ is $-CH_2OR_{10}$ or $-CH_1OSi(G_1)_3$, wherein $R_{10}$ and $G_1$ are as defined above.

$X_3$ is a carboxylic ester within the scope of $-COOR_1$, a primary alcohol of the formula $-CH_2OH$ or its corresponding $R_{10}$ ether, $-CH_2NL_2L_3$, $-COL_4$, or tetrazolyl, wherein $R_1$, $R_{10}$, $L_2$, $L_3$, and $L_4$ are as defined above.

With respect to Chart A, a method is provided whereby an alkyne addition to the formula XXI lactol yields a 6-keto-PGF-type intermediate which is thereafter transformed to a formula XXX prostaglandin analog.

With respect to the various compounds of formula XXI, these compounds are known in the art or prepared by methods described by the prior art. In particular, see United States Pat. No. 4,081,803, describing such intermediates wherein $Y_2$ is $-CH=C(Hal)-$; United States Pat. No. 4,026,909, describing formula XXI compounds wherein $Y_2$ is cis—CH=CH—; and U.S. Pat. No. 4,013,695, describing formula XXI compounds wherein $Y_2$ is trans-CH=CH-.

The formula XXI compound is thereafter transformed to the formula XXII compound by an alkyne addition, employing conditions described in United States Pat. No. 4,013,695 for such transformation. Accordingly, this alkyne addition proceeds by reacting the appropriate ω-(tri-substituted silyl)oxy-alkyne, HC≡C-$Z_2X_2$, with the formula XXI compound in the presence of an organolithium compound, e.g., methyl lithium.

The formula XXIII compound is then prepared from a formula XXII compound by acylation of the C-9 hydroxy. This acylation proceeds by methods known in the art for introducing acyl protecting groups according to $R_9$. See the reference provided above. Thereafter, the formula XXIV compound is prepared from the formula XXIII compound by a selective catalytic hydrogenation of the acetylenic bond. This catalytic hydrogenation employs a conventional catalyst for this purpose (e.g., paladium on carbon) and proceeds under a hydrogen atmosphere at about atmospheric pressure. Reaction is maintained until about two equivalents of hydrogen are absorbed, at which time the formula XXIV product is recovered from the mixture of hydrogenated formula XXIII products obtained.

The formula XXV compound is then prepared from the formula XXIV compound by reduction of the 6-oxo-PGF-type formula XXIV compounds to corresponding 6-hydroxy-PGF-type intermediate. For this purpose, known reducing agents, e.g., sodium borohydride, are successfully employed. Reaction is maintained at or below 0° C. (preferably between $-10°$ and $-20°$ C.) until thin layer chromatographic analysis indicates the reduction to be complete. The formula XXV compound is then transformed to the corresponding formula XXVI compound by replacing the hydrogen of the C-6 hydroxy with a blocking group according to $R_{10}$. Conveniently, the $R_{10}$ blocking group selected is the same as that of the $R_{36}$ or $M_6$ moiety. Conventional methods for the introduction of such blocking groups, as described above, are employed.

The formula XXVI compound is then transformed to the formula XXVII compound by first hydrolyzing the silyl ether and thereafter oxidizing the resulting primary alcohol to a carboxylic acid. The silyl ether hydrolysis proceeds selectively, employing tetra-n-butylammonium fluoride. See Corey, JACS 94:6190 (1972).

The primary alcohol thereby obtained is oxidized to the corresponding formula XVII PGF-type carboxylic acid. Reagents employed in this oxidation are, for example, those described in U.S. Pat. No. 4,013,695 for the analagous transformation therein. In particular, the Adams catalyst (a hydrogen-reduced aqueous suspension of platinum dioxide) or alternatively the Jones reagent is employed. See Fieser and Fieser, Reagents for Organic Synthesis, New York, New York, 1977, page 890, for a discussion of the preparation of the Adam's catalyst.

The formula XXVII compound is then transformed to the formula XXVIII compound by deacylation, followed by dehydrohalogenation. For deacylation, basic saponification (i.e., sodium hydroxide) is employed, while a strong organic base is used for dehydrohalogenation. The formula XXIX PGE-type compound is then prepared, by oxidation of the corresponding PGF-type compound.

The formula XXX compound is then prepared from the formula XXIX compound by hydrolysing the blocking groups according to $R_{10}$, under acidic conditions as described above. Further, the formula XXX esters and salts are prepared by esterification and neutralization with base of the formula XXIX free acid, employing methods known in the art. See U.S. Pat. No. 4,016,184.

Chart B provides a method whereby the preparation of the formula XL products proceed from the formula XXXI PGF$_2$α-type, 11,15-bis(ether).

The various compounds of formula XXXI are known in the art or are readily available by methods known in the art. These compounds are available as bis ethers, as depicted, or are optionally available in the form of the corresponding dihydroxy compounds, which are subsequently etherified.

The formula XXXII compound is prepared from the formula XXXI compound by halocyclization. When $R_{16}$ of the formula XXXII compound is iodo, this halocyclization proceeds by reacting the formula XXXI compound with potassium iodide or an alkali metal carbonate or bicarbonate and an organic system containing iodine. In the latter case, solvents such as methylene chloride are employed. Further, reaction temperatures at or below ambient temperature, preferably about 0° C., are employed. The reaction is then quenched by addition of sodium sulfate and sodium carbonate yielding the formula XXXII iodo compounds. When $R_{16}$ is bromo, a convenient brominating agent is N-bromosuccinimide. Solvents such as methylene chloride are employed and the reaction allowed to proceed between about 0° C. and ambient temperature.

The formula XXXII products are recovered by conventional means. However, high pressure liquid chromatographic separation is an especially convenient technique for isolating a pure formula XXXII product.

The formula XXXIII compound is then prepared from the formula XXXII compound by dehydrohalogenation. Such a dehydrohalogenation proceeds by reacting the formula XXXII compound with a dehydrohalogenating agent such as are described in Fieser and Fieser, Reagents for Organic Synthesis, page 1308, John Wiley & Sons, Inc., New York, New York (1967). The preferred dehydrohalogenation agents for the present transformation are tertiary amines and sodium or potassium superoxides, carbonates, hydroxides, benzoates, acetates, trifluoroacetates, or carbonates. Further, silver acetate and tetraalkyl ammonium superoxides are also employed. Among the tertiary amines are 1,5-diazobicyclo[4.3.0]nonene-5 and 1,5-diazobicyclo[5.4.0]undecene-5 (DBN and DBU respectively). For a discussion of use of the superoxides described above see Johnson, et al., Journal of Organic Chemistry 40:1680 (1975) and Dietz, et al., Journal of the Chemical Society (B), 1970, pages 816-820.

The formula XXXIV compound is then prepared from the formula XXXIII compound by decyclizing the formula XXXIII enol ether under aqueous acidic conditions to the corresponding hydroxy-ketone of formula XXXIV. Suitable acids for this decyclization are dilute hydrochloric, perchloric, or sulfuric acid.

The formula XXXIV compound is then successively deacylated at C-9, yielding the formula XXXV compound; reduced at C-6 from a ketone to an alcohol, yielding the formula XXXVI compounds; etherified with an $R_{10}$ blocking group at C-6, yielding the formula XXXVII compound; deacylated at C-9, yielding the formula XXXVIII compound; oxidized at C-9 to PGE-type compound, yielding the formula XXXIX compound; and hydrolyzed under acidic conditions, yielding the formula XL compound. Each of these transformations is respectively analogous to those described in Chart A for the transformation of the 6-oxo-PGF-type compound of formula XXII successively to the formula XXIII C-9 acylate, the formula XXV C-6 alcohol, the formula XXVI C-6 ether, the formula XXVII C-9 free hydroxy, the formula XXIX PGE-type compound, and the formula XXX deetherified compound.

With respect to Chart C, a method is provided whereby 6-oxo-PGF$_1$-type compounds are transformed to corresponding 6-hydroxy-PGE$_1$-type compounds.

With respect to Chart C the formula 6-oxo-PGF$_1$α-type compound is prepared by methods known in the art or is itself known in the art. See, for example, methods for the preparation of corresponding bis-THP ethers in Charts A and B.

The formula XLI compound is thereafter selectively silylated, whereby secondary and primary hydroxyls other than the C-9 hydroxy are transformed to corresponding silyl derivatives. This selective silylation is accomplished by methods known in the art. See for example the silylation of certain prostaglandins and analogs thereof in U.S. Pat. Nos. 3,892,792 and 3,822,303.

Thereafter, the preparation of the C-9 acylate of formula XLIII is accomplished by methods described in Chart A. Thereafter the formula XLIV compound is prepared by hydrolysis of the silyl groups yielding the PGF-type, 9-acylate. This hydrolysis is accomplished using mild acidic conditions (e.g., dilute aqueous mineral acid), as is known in the art.

The formula XLIV 6-oxo-PGF-type commpound is then transformed to the formula XLV 6-hydroxy-PGF-type compound by reduction, as described in Chart A. Thereafter the various hydroxyls of the formula XLV compounds are transformed to corresponding $R_{10}$ ethers, employing methods described in Chart A. Thereafter this formula XLVI compound is successively transformed to the formula XLVII, formula XLVIII and formula XLIX compounds, employing analogous methods described in Chart A (i.e., the transformation of the formula XXVI compound therein to the formula XXX compound.

When the compounds above are prepared as esters and acids are desired, enzymatic deesterification yields the corresponding carboxylic acid. See. U.S. Pat. No. 3,761,356, describing an esterase preparation. For the acids thusly prepared, the corresponding pharmacologically acceptable salts thereof are prepared by neutralization with the base corresponding to the salt to be prepared.

With respect to the novel PG-type amides ($X_1$ is -COL$_4$) and p-substituted phenyl esters ($R_1$ is p-substituted phenyl), such compounds are prepared as follows:

With regard to the preparation of the p-substituted phenyl esters disclosed herein, such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amino and cycloamino derivatives.

This PG-type anhydride is then reacted with a solution of the phenol corresponding to the p-substituted phenyl ester to be prepared. This reaction proceeds preferably in the presence of a tertiary amine such as pyridine. When the conversion is complete, the p-substituted phenyl ester has been recovered by conventional techniques.

Having prepared the PGF-type carboxylic acids, the corresponding carboxyamides are prepared by one of several amidation methods known in the prior art. See, for example, U.S. Pat. No. 3,981,868, issued Sept. 21, 1976 for a description of the preparation of the present amino and cycloamino derivatives of prostaglandin-type free acids and U.S. Pat. No. 3,954,741 describing the preparation of carbonylamino and sulfonylamino derivatives of prostaglandin-type free acids.

The preferred method by which the present amino and cycloamino derivatives of the PGF-type acids are prepared is, first by transformation of such free acids to corresponding mixed acid anhydrides. By this procedure, the prostaglandin-type free acid is first neutralized with an equivalent of an amine base, and thereafter reacted a slight stoichiometric excess of a chloroformate corresonding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the PGF-type free acid is mixed with both the tertiary amine base and the chloroformate in a suitable solvent (e.g., aqueous tetrahydrofuran), allowing the reaction to proceed at −10° to 20° C.

Thereafter, the mixed anhydride is converted to the corresponding amino or cycloamino derivative by reaction with the amine corresponding to the amide to be prepared. In the case where the simple amide (—NH₂) is to be prepared, the transformation proceeds by the addition of ammonia. Accordingly, the corresponding amine (or ammonia) is mixed with the mixed anhydride at or about −10° to +10° C., until the reaction is shown to be complete. For highly volatile amines, acid addition salts thereof (e.g., methylamine hydrochloride) are employed in place of the corresponding free base (e.g., methylamine).

Thereafter, the novel PGF-type amino or cycloamino derivative is recovered from the reaction mixture by conventional techniques.

The carbonylamino and sulfonylamino derivatives of the presently disclosed PG-type compounds are likewise prepared by known methods. See, for example, U.S. Pat. No. 3,954,741 for description of the methods by which such derivatives are prepared. By this known method, the prostaglandin-type free acid is reacted with a carboxyacyl of sulfonyl isocyanate, corresponding to the carbonylamino or sulfonylamino derivative to be prepared.

By another, more preferred method the sulfonylamino derivatives of the present compounds are prepared by first generating the PG-type mixed anhydride, employing the method described above for the preparation of the amino and cycloamino derivatives. Thereafter, the sodium salt of the corresponding sulfonamide is reacted with the mixed anhydride and hexamethylphosphoramide. The pure PG-type solfonylamido derivative is then obtained from the resulting reaction mixture by conventional techniques.

The sodium salt of the sulfonamide corresponding to the sulfonylamino derivative to be prepared is generated by reacting the sulfonamide with alcoholic sodium methoxide. Thus, by a preferred method methanolic sodium methoxide is reacted with an equal molar amount of the sulfonamide. The sulfonamide is then reacted, as described above, with the mixed anhydride, using about four equivalents of the sodium salt per equivalent of anhydride. Reaction temperatures at or about 0° C. are employed.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, and T-60 spectrophotometer on deuterochloroform solutions with tetramethylsilane as an internal standard (downfield).

Mass spectra are recorded on an CEC model 21-110B Double Focusing High Resolution Mass Spectrometer on an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column.

"Brine", herein, refers to an aqueous saturated sodium chloride solution.

The A-1X solvent system used in thin layer chromatography is made up from ethyl acetate-acetic acid-cyclohexane-water (90:20:50:100) as modified from M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and inpurities).

Melting points (MP) are determined on a Fisher-Johns or Thomas-Hoover melting point apparatus.

DDQ refers to 2,3-dichloro-5,6-dicyano-1,4-benzoquinone.

Preparation 1
(5R,6R)-5-Iodo-9-deoxy-6,9α-epoxy-PGF$_1$, 11,15-Bis(tetrahydropyranyl ether), Methyl Ester, and (5S,6S)-5-Iodo-9-deoxy-6,9α-epoxy-PGF$_1$, 11,15-Bis(tetrahydropyranyl ether), Methyl Ester. (Formula XXXII: X$_3$ is —COOCH$_3$, Z$_1$ is —(CH$_2$)$_3$—, R$_{16}$ is iodo, R$_{38}$ is —OTHP, Y$_1$ is trans—CH=CH—, M$_6$ is

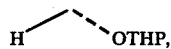

R$_3$ and R$_4$ of the L$_1$ moiety are hydrogen; and R$_7$ is n-butyl).

A. A suspension of the PGF$_2$α, methyl ester (3.0 g.) in 60 ml. of water is treated with sodium carbonate (1.7 g.) and cooled in an ice bath. To the resulting solution is added potassium iodide (2.7 g.) and iodine (4.14 g.) and stirring continued for 3 hr. at about 0° C. Thereafter sodium sulfite (2.5 g.) and sodium carbonate (0.8 g.) are added to decolorize the mixture. After a few minutes the mixture is extracted with chloroform. The organic phase is washed with brine, dried over sodium sulfate, and concentrated to yield the diol corresponding to the title compound, an oil, which is further purified by silica gel chromatography, eluting with methylene chloride (15–50%)-acetone to yield the less polar (5S,6S) diol, 0.29 g. and the more polar (5R,6R) diol, 3.36 g.

B. A solution of the reaction product of part A (10 g.) in dichloromethane (20 ml.) is treated with dihydropyran (9.1 ml., 8.4 g.) and dichloromethane saturated with pyridine hydrochloride (10 ml.). The reaction proceeds at ambient temperature for 4.5 hr. whereupon silica gel TLC indicates the reaction to be complete. The resulting mixture is then diluted with diethyl ether, washed with 5% aqueous sodium chloride and 5% aqueous sodium bicarbonate, dried and concentrated under reduced pressure to yield a viscous residue (14.3 g.) which is chromatographed on silica gel eluting with Skellysolve-B and ethyl acetate (3:1). Accordingly there is obtained 8.44 g. of pure title product.

EXAMPLE 1
6-hydroxy-PGE$_1$ (Formula IV: X$_1$ is —COOH, Z$_1$ is —(CH$_2$)$_3$—, R$_8$ is hydroxy, Y$_1$ is trans—CH=CH—, R$_3$ and R$_4$ of the L$_1$ moiety and R$_5$ of the M$_1$ moiety are all hydrogen, and R$_7$ is n-butyl.)

Refer to Chart B.

A. The title product of Preparation 1 (1.77 g.) in tetrahydrofuran (10 ml.) is treated with DBU (470 g.) at ambient temperature. After about 20 min. precipitation of DBU hydroiodide begins and formation of the title product is noted by silica gel TLC. When the reaction is shown to be complete by silica gel TLC (in about 2 days, with addition of 0.470 g. of additional DBU after 16 hrs.), the resulting suspension is cooled and the precipitates filtered and the filtrate washed successively with 0.02 ml. aqueous potassium bisulfate, 5% aqueous sodium chloride, and 5% aqueous sodium bicarbonate, dried, and evaporated under reduced pressure. Accordingly there is obtained crude formula XXXIII product, PGI$_2$, methyl ester, 11,15-bis(tetrahydropyranyl ether).

B. The crude formula XXXIII product of part A in 25 ml. of methylene chloride is treated with 4% aqueous acetic acid (2 ml.) for 1.5 hr. Thereafter an additional 4% aqueous acetic acid (5 ml.) is added, the reaction yielding the corresponding formula XXXIV compound being complete within about 1 hr. This formula XXXIV compound, 6-oxo-PGF$_1$α, methyl ester, 11,15(bis-tetrahydropyranyl ether), 1.226 g., is then recovered in crude form.

C. The crude reaction product of part B is then dissolved in 10 ml. of pyridine and treated with acetic anhydride (5 ml.) at ambient temperature for 15 hr. The resulting formula XXV acrylate is then isolated, yielding 1.28 g. of 6-oxo-PGF$_1$α, methyl ester, 9acetate, 11,15-bis(tetrahydropyranyl ether).

D. The reaction product of part C (1.11 g.) in methanol (20 ml.) at −25° C. is treated with sodium borohydride (0.4 g.) for 25 min. Thereafter the resulting mixture is diluted with diethyl ether and treated dropwise with acetic acid until the reaction is fully quenched. The resulting mixture is then washed successively with 0.2 M aqueous potassium bisulfate, 5% aqueous sodium hydroxide, and 5% aqueous sodium bicarbonate; dried; and concentrated under reduced pressure to a colorless residue (1.16 g.). This residue, crude formula XXXVI product, is then chromatographed on silica gel (60 g.), eluting with Skellysolve-B and ethyl acetate (7:3), yielding 1.11 g. of pure (6RS)-6-hydroxy-PGF$_1$α, methyl ester, 9-acetate, 9,11-bis(tetrahydropyranyl ether).

E. The reaction product of part B (1.11 g.) in methylene chloride (10 ml.) is treated with 20 ml. of dichloromethylene saturated with pyridine hydrochloride and 2 ml. of dihydropyran. After 13 hr. the resulting mixture is diluted with diethyl ether, washed successively with 5% aqueous sodium bicarbonate, 0.2 M aqueous potassium biculfate and 5% aqueous sodium chloride; dried; and evaporated to yield 1.988 g. of (6RS)-6-hydroxy-PGF$_1$α, methyl ester, 9-acetate, 6,11,15-tris(tetrahydropyranyl ether), a formula XXXVII compound.

F. The reaction product of part E (1.1988 g.) is diluted with methanol and concentrated to remove chlorinated solvents (e.g., chloroform and carbon tetrachloride). The resulting residue is then dissolved in methanol (35 ml.) and treated with 2 N aqueous sodium hydroxide (10 ml.). The resulting mixture is then maintained at ambient temperature for 20 hr. whereupon dilution with water and acidification with cold dilute aqueous phosphoric acid yields an oily precipitate which is extracted with diethyl ether. Drying and evaporating under reduced pressure yields 1.02 g. of crude formula XXXVIII compound: (6RS)-6-hydroxy-PGF$_1$α, 6,11,15-tris(tetrahydropyranyl ether). Chromatography on silica gel (60 g.), eluting with Skellysolve-B and ethyl acetate (7:3) and (3:2) yields 0.967 g. of pure product.

F. The reaction product of part E (0.967 g.) in acetone at −15° C. is treated dropwise with excess Jones reagent (2.7 M; 0.65 ml.) with vigorous stirring. The reaction is allowed to proceed at −10° C. for 14 min. whereupon excess reagent is destroyed by dropwise addition of isopropanol. The resulting suspension is then diluted with ethyl ether and washed with 5% aqueous sodium chloride, dried, and concentrated under reduced pressure to yield 0.8254 g. of formula XXXIX compound: (6RS)-6-hydroxy-PGF$_1$α, 6,11,15-tris(tetrahydropyranyl ether).

G. The reaction product of part F (0.825 g.) in acetic acid (20 ml. and water (10 ml.) is heated to 43° C. for 3 hr. The resulting solution is then diluted with water (25 ml.) and lyophilized for 22 hr. The residue, containing acetic acid, is then concentrated under reduced pressure to yield 0.7082 g. of crude title product, the formula XL compound: (6RS)-6-hydroxy-PGE$_1$.

Chromatographing the crude product, eluting with ethyl acetate and hexane (3:1) yields 0.4228 g. of pure title product.

Reacting the title product of Example 1 with ethereal diazomethane yields the corresponding methyl ester: (6RS)-6-hydroxy-PGE$_1$, methyl ester.

Using high pressure liquid chromatography, the respective isomers of the above free acids or their corresponding methyl esters are separated, yielding pure (6S) and (6R) material.

Further following the procedure of Example 1 but employing the various PGF$_2\alpha$-type compounds of formula XXXI in place of PGF$_2\alpha$, methyl ester, 11,15-bis(-tetrahydropyranyl ether), ether are obtained the various corresponding formula XL products.

EXAMPLE 2

6-hydroxy-13,14-didehydro-PGE$_1$ (Formula IV: X$_1$ is —COOH, Z$_1$ is —(CH$_2$)$_3$—, R$_8$ is hydroxy, Y$_1$ is —C≡C—, R$_3$ and R$_4$ of the L$_1$ moiety and R$_5$ of the M$_1$ moiety are hydrogen, and R$_7$ is n-butyl.)

Refer to Chart A.

A. 3α-tetrahydropyranyloxy-5α-hydroxy-2β-(2-chloro-3α-tetrahydropyranyloxy-trans-1-octenyl)-1α-cyclopentaneacetic acid γ-lactone (6.4 g.) in tetrahydrofuran (40 ml.) is added to a solution of lithium 3-(t-butyldimethylsilyloxy)propylacetylide prepared from 30 g. 1-(t-butyldimethylsilyloxy)-4-pentyne as described in Example 14, part B of U.S. Pat. No. 4,013,695. Reaction conditions of −10° C. are then maintained for 30 min. whereupon the resulting mixture is warmed to ambient temperature and reacted for an additional 80 min. Thereupon the resulting solution is treated with ammonium chloride and 0.2 M aqueous potassium bisulfate, added dropwise at 0° C. The resulting mixture is then diluted with diethyl ether and washed successively with 5% aqueous sodium chloride, 5% aqueous sodium bicarbonate, and 0.2 M potassium bisulfate; dried; and concentrated under reduced pressure to yield 9.71 g. of crude formula XXXII product. This crude product is then chromatographed on silica gel, eluting with ethyl acetate and Skellysolve-B (17:3) yielding 2.73 g. of pure 2-decarboxy-2(t-butyldimethylsilyloxy)methyl-4,4,5,5-tetradehydro-5-hydroxy-14-chloro-PGF$_1\alpha$, 11,15-bis(-tetrahydropyranyl ether).

B. The reaction product of part A (3.40 g.) in pyridine (5 ml.) is treated with acetic anhydride (2.5 ml.) for 20 hr. at ambient temperature. The resulting mixture is then diluted with water and extracted with diethyl ether. The ethereal extracts are then washed successively with 5% aqueous sodium chloride, 5% aqueous sodium bicarbonate, and 0.2 M aqueous potassium bisulfate, dried, and concentrated under reduced pressure to yield 0.239 g. of formula XXIII acylate: 2-decarboxy-2-(t-butyldimethylsilyloxy)methyl-4,4,5,5-tetradehydro-6-oxo-14-chloro-PGF$_1\alpha$, 9-acetate, 11,15-bis(tetrahydropyranyl ether).

C. The reaction product of part B (2.24 g.) in ethyl acetate (60 ml.) is treated with a 10% palladium on carbon catalyst (0.28 g.) under a hydrogen atmosphere (atmospheric pressure) for 100 min. After uptake of about 145 ml. of hydrogen, the resulting solution is filtered and evaporated to yield a viscous oil (2.186 g.) A second hydrogenation of 2.89 g. of the reaction product of part B yields a similar 2.26 g. sample of the hydrogenated oil. Chromatography on silica gel yields pure formula XXIV product: 2-decarboxy-2-(t-butyldimethylsilyloxy)methyl-14-chloro-PGF$_1\alpha$, 9-acetate, 11,15-bis(tetrahydropyranyl ether). D. A solution of the reaction product of part C (2 g.) in methanol (40 ml.) at −15° C. is treated with sodium borohydride (0.075 g.) for 35 min. The reaction is thereafter quenched by dropwise addition of acetic acid and the resulting solution diluted with diethyl ether, successively washed with 0.2 M aqueous potassium bisulfate and 5% aqueous sodium bicarbonate, dried, and concentrated under reduced pressure to yield 2.0 g. of formula XXV compound: 2-decarboxy-2-(t-butyldimethylsilyloxy)methyl-5-hydroxy-14-chloro-PGF$_1\alpha$, 9-acetate, 11,15-bis(tetrahydropyranyl ether).

E. The crude product obtained in part D (2.0 g.) in dichloromethane (10 ml.) is then treated with dihydropyran (2 ml.) and 20 ml. of dichloromethane saturated with pyridine hydrochloride. Reaction conditions are maintained for 18 hr., whereupon pure formula XXVI compound is isolated, 2.3 g of 2-decarboxy-2-(t-butyldimethylsilyloxy)methyl-6-hydroxy-14-chloro-PGF$_1\alpha$, 9-acetate, 6,11,15-tris(tetrahydropyranyl ether).

F. The reaction product of part E (2.26 g.) in dry tetrahydrofuran (20 ml.) is treated with tetra-n-butylammonium fluoride (4.7 ml.) of a 4.2 M solution in tetrahydrofuran and reacted at ambient temperature for 1.5 hr. The resulting solution is then diluted with diethyl acetate, washed successively with 0.2 M potassium bisulfate, 5% aqueous sodium chloride, 5% aqueous sodium bicarbonate, and water; dried; and concentrated to a dark oil. The oil is then evaporated from 600 ml. of benzene (to remove the fluoride reagent) and thereafter chromatographed on 60 g. of silica gel eluting with ethyl acetate and hexane (1:1) yielding 1.5262 g. of pure 2-decarboxy-2-hydroxymethyl-6-hydroxy-14-chloro-PGF$_1\alpha$, 9-acetate, 6,11,15-tris(tetrahydropyranyl ether), the primary alcohol corresponding to formula XXVI.

G. The solution of the reaction product of part F (1.53 g.) in acetone (35 ml.) at −10° C. is treated dropwise with Jones reagent, (1.66 ml. of 2.67 M) and after reaction at 14 min. at ambient temperature, the resulting mixture is then quenched by dropwise addition of isopropanol diluted with diethyl ether, washed with 5% aqueous sodium chloride, dried, and evaporated under reduced pressure to yield 2.11 g. of a pale oil, the formula XXVII compound.

H. The reaction product of part G (1.55 g.) in methanol (10 ml.) is treated with 2 N aqueous sodium hydroxide (5 ml.) and water (5 ml.). The solution is then stirred for about 10 hr. at ambient temperature and thereafter cooled and acidified with cold dilute phosphoric acid. The resulting suspension is then extracted with diethyl ether and benzene (1:1) and the combined organic extract washed with 5% aqueous sodium chloride, dried, and evaporated under reduced pressure to yield 1.31 g. of 6-hydroxy-14-chloro-PGF$_1\alpha$, 6,11,15-tris(tetrahydropyranyl ether).

I. Dimsyl sodium (prepared from a 50% mineral oil dispersion of sodium hydride, 2.93 g., in dimethyl sulfoxide, 15 ml., by reaction at 65°–70° C. for 90 min.) is added to a solution of the reaction product of part H (1 g.) yielding a gummy precipitate which is soluble in dimethyl sulfoxide 910 ml.) and tetrahydrofuran (20 ml.) on stirring at ambient temperature for several minutes. After 17 hr., the resulting dark solution is treated with 0.2 M aqueous potassium bisulfate, extracted with diethyl ether and ethyl acetate, and the organic extracts concentrated to yield 0.883 g. of crude 6-hydroxy-13,14-didehydro-PGF$_1\alpha$, 6,11,15-tris(tetrahydropyranyl ether). Chromatographing on acid washed silica gel, eluting with ethyl acetate and hexane (1:1) yields 0.42 g. of pure product.

J. The reaction product of part I (1.49 g.) and acetone (7 ml.) is treated at $-18°$ C. with Jones reagent (0.3 ml.) for 20 min. The reaction is quenched by dropwise addition of isopropanol and the resulting mixture diluted with diethyl ether, decanted from the deposited solids, washed with water, dried and evaporated to yield a pale yellow residue (0.133 g.)., 6-hydroxy-13,14-didehydro-PGE$_1$, 6,11,15-tris(tetrahydropyranyl ether).

K. The crude product of part J (0.133 g.) and acetic acid (6 ml.) and water (3 ml.) is heated to 45° C. for 2.5 hr. Thereafter the resulting mixture is diluted with water (20 ml.) and lyophilized. The residue (0.109 g.) is then chromatographed on acid washed silica gel, eluted with ethyl acetate and hexane (3:2) yielding 66 mg. of pure title product as a mixture of (6S) and (6R) isomers.

The isomerically pure product is obtained from the above mixture of Example 2 title products by high pressure liquid chromatographic separation.

The corresponding methyl esters are obtained by reaction with ethereal diazomethane.

Further following the procedure of Chart A, there are obtained the various 6-hydroxy-13,14-didehydro-PGE-type compounds of formula XXX from the corresponding formula XXI intermediates.

With further respect to Example 2, the part G product exhibits a high resolution mass spectral peak for the trimethylsilyl derivative at 671.3707 and other peaks at 587, 502, and 85. Infrared absorptions are observed at 2700–3200, 2990, 2850, 1740, and 1690 cm$^{-1}$. NMR absorptions are observed at 1.05–1.95, 2.10, 2.1–2.8, 3.0–5.4, 5.4–5.9, and 11.25 $\delta$.

For the product of Example 2, part I, the high resolution mass spectrum for the trimethylsilyl derivative exhibits a peak at 664.4233 and other peaks at 751, 681, 649, 580, 563, and 85. Infrared absorptions are observed at 3350–3400, 2900, 2850, 2600–3200, 2220, 1700, and 1740 cm$^{-1}$. Characteristic NMR absorptions are observed at 0.90, 1.05–2.9, and 3.1–5.1 $\delta$.

With respect to the reaction product of Example 2, part J, a high resolution mass spectrum for the trimethylsilyl derivative is observed at 590.3657 and other peaks at 575, 506, 489, 405, and 85. Infrared absorptions are observed at 2600–3200, 2850, 2900, 2200, 1700, 1740, 1195, 1150, 1125, 1110, 1050, 1030, and 1020 cm$^{-1}$. NMR absorptions are observed at 0.90, 1.1–3.2, 3.2–5.05, and 10.10 $\delta$.

With respect to the title product of Example 2, the mass spectrum for the trimethylsilyl derivative exhibits a high resolution peak at 656.3748 and other peaks at 641, 585, 566, 557, 540, 289, and 275. Infrared absorptions are observed at 3300–3400, 2800, 2850, 2220, and 1740 cm$^{-1}$. NMR absorptions are observed at 0.90, 1.05–3.0, 3.67–4.5, and 4.6–5.6 $\delta$.

Following the procedure of the above examples, but employing the appropriate starting material, there are prepared
 (6S)-6-hydroxy-PGE$_1$-type compounds;
 (6R)-6-hydroxy-PGE$_1$-type compounds; or
 (6RS)-6-hydroxy-PGE$_1$-type compounds in free acid, amide, or ester form which exhibit the following side chain substituents:
15-Methyl;
16-Methyl;
15,16-Dimethyl-;
16,16-Dimethyl-;
16-Fluoro-;
15-Methyl-16-fluoro-;
16,16-Difluoro-;
15-Methyl-16,16-difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-Methyl-17-phenyl-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenyl-17,18,19,20-tetranor-;
15-Methyl-16-phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-Phenyl-18,19,20-trinor-;
15-Methyl-16-phenyl-18,19,20-trinor-;
16-Methyl-16-phenyl-18,19,20-trinor-;
15,16-Dimethyl-16-phenyl-18,19,20-trinor-;
16-Phenoxy-17,18,19,20-tetranor-;
15-Methyl-16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
15-Methyl-16-phenoxy-18,19,20-trinor-;
16-Methyl-16-phenoxy-18,19,20-trinor-;
15,16-Dimethyl-16-phenoxy-18,19,20-trinor-;
13,14-Didehydro-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenyl-17,18,19,20-tetranor-13,14-didehydro-;
16-(m-trifluoromethylphenyl)-17,18,19,20-tetranor-13,14-didehydro-;
16-(m-chlorophenyl)-17,18,19,20-tetranor-13,14-didehydro-;
16-Phenyl-18,19,20-trinor-13,14-didehydro-;
16-Methyl-16-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor-13,14-didehydro-;
16(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
16-Methyl-13,14-dihydro-;
16,16-Dimethyl-13,14-dihydro-;

16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
13-cis-;
16-Methyl-13-cis-;
16,16-Dimethyl-13-cis-;
16-Fluoro-13-cis-;
16,16-Difluoro-13-cis-;
17-Phenyl-18,19,20-trinor-13-cis-;
17-(m-trifluoromethylphenyl)-18,19,20-trinor-13-cis-;
17-(m-chlorophenyl)-18,19,20-trinor-13-cis-;
17-(p-fluorophenyl)-18,19,20-trinor-13-cis-;
16-Methyl-17-phenyl-18,19,20-trinor-13-cis-;
16,16-Dimethyl-17-phenyl-18,19,20-trinor-13-cis-;
16-Fluoro-17-phenyl-18,19,20-trinor-13-cis-;
16,16-Difluoro-17-phenyl-18,19,20-trinor-13-cis-;
16-Phenyl-17,18,19,20-tetranor-13-cis-;
16-(m-trifluoromethylphenyl)-17,18,19,20-tetranor-13-cis-;
16-(m-chlorophenyl)-17,18,19,20-tetranor-13-cis-;
16-(p-fluorophenyl)-17,18,19,20-tetranor-13-cis-;
16-Phenyl-18,19,20-trinor-13-cis-;
16-Methyl-16-phenyl-18,19,20-trinor-13-cis-;
16-Phenoxy-17,18,19,20-tetranor-13-cis-;
16-(m-trifluoromethylphenoxy)-17,18,19,20-tetranor-13-cis-;
16-(m-chlorophenoxy)-17,18,19,20-tetranor-13-cis-;
16-(p-fluorophenoxy)-17,18,19,20-tetranor-13-cis-;
16-Phenoxy-18,19,20-trinor-13-cis-;
16-Methyl-16-phenoxy-18,19,20-trinor-13-cis-;
2,2-Difluoro-;
2,2-Difluoro-15-methyl-;
2,2-Difluoro-16-methyl-;
2,2-Difluoro-16,16-dimethyl-;
2,2-Difluoro-16-fluoro-;
2,2-Difluoro-16,16-difluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2-Difluoro-16-fluoro-17-phenyl-18,19,20-trinor-;
2,2-Difluoro-16,16-difluoro-17-phenyl-18,19,20-trinor-;
2,2-Difluoro-16-phenyl-17,18,19,20-tetranor-;
2,2-Difluoro-16-(m-trifluoromethylphenyl)-17,18,19,20-tetranor-;
2,2-Difluoro-16-(m-chlorophenyl)-17,18,19,20-tetranor-;
2,2-Difluoro-16-(p-fluorophenyl)-17,19,19,20-tetranor-;
2,2-Difluoro-16-phenyl-18,19,20-trinor-;
2,2-Difluoro-16-methyl-16-phenyl-18,19,20-trinor-;
2,2-Difluoro-16-phenoxy-17,18,19,20-tetranor-;
2,2-Difluoro-16-(m-trifluoromethylphenoxy)-17,18,19,20-tetranor-;
2,2-Difluoro-16-(m-chlorophenoxy)-17,18,19,20-tetranor-
2,2-Difluoro-16-(p-fluorophenoxy)-17,18,19,20-tetranor-
2,2-Difluoro-16-phenoxy-18,19,20-trinor-;
2,2-Difluoro-16-methyl-16-phenoxy-18,19,20-trinor-;
2,2-Difluoro-16-methyl-13,14-didehydro-;
2,2-Difluoro-16,16-dimethyl-13,14-didehydro-;
2,2-Difluoro-16-fluoro-13,14-didehydro-;
2,2-Difluoro-16,16-difluoro-13,14-didehydro-;
2,2-Difluoro-17-phenyl-18,19,20-trinor-13,14-didehydro-
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Difluoro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenyl-17,18,19,20-tetranor-13,14-didehydro-;
2,2-Difluoro-16-(m-trifluoromethylphenyl)-17,18,19,20-tetranor-13,14-didehydro-;
2,2-Difluoro-16-(m-chlorophenyl)-17,18,19,20-tetranor-13,14-didehydro-;
2,2-Difluoro-16-phenyl-18,19,20-trinor-13,14-didehydro-
2,2-Difluoro-16-methyl-16-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethylphenoxy)-17,18,19,20-tetranor-13,14-didehydro-;
2,2-Difluoro-16-(m-chlorophenoxy)-17,18,19,20-tetranor-13,14-didehydro-;
2,2-Difluoro-16-phenoxy-18,19,20-trinor-13,14-didehydro
2,2-Difluoro-16-methyl-16-phenoxy-18,19,20-trinor-13,14-didehydro-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
2,2-Difluoro-17-phenyl-18,19,20-trinor-13,14-dihydro-;

2,2-Difluoro-17-(m-trifluoromethylphenyl)-18,19,20-trinor-13,14-dihydro-;
2,2-Difluoro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2-Trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenyl-17,18,19,20-tetranor-13,14-dihydro-;
2,2-Difluoro-16-(m-trifluoromethylphenyl)-17,18,19,20-tetranor-13,14-dihydro-;
2,2-Difluoro-16-(m-chlorophenyl)-17,18,19,20-tetranor-13,14-dihydro-;
2,2-Difluoro-16-(p-fluorophenyl)-17,18,19,20-tetranor-13,14-dihydro-;
2,2-Difluoro-16-phenyl-16-phenyl-18,19,20-trinor-13,14-dihydro-;
2,2-Difluoro-16-methyl-16-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;
2,2-Difluoro-16-(m-chlorophenoxy)-17,18,19,20-tetranor-13,14-dihydro-;
2,2-Difluoro-16-(p-fluorophenoxy)-17,18,19,20-tetranor-13,14-dihydro-;
2,2-Difluoro-16-phenoxy-18,19,20-trinor-13,14-dihydro-
2,2-Difluoro-16-methyl-16-phenoxy-18,19,20-trinor-13,14-dihydro-;
2,2-Difluoro-13-cis-;
2,2-Difluoro-16-methyl-13-cis-;
2,2-Difluoro-16,16-dimethyl-13-cis-;
2,2,16-Trifluoro-13-cis-;
2,2,16,16-Tetrafluoro-13-cis-;
2,2-Difluoro-17-phenyl-18,19,20-trinor-13-cis-;
2,2-Difluoro-17-(m-trifluoromethylphenyl)-18,19,20-trinor-13-cis-;
2,2-Difluoro-17-(m-chlorophenyl)-18,19,20-trinor-13-cis-;
2,2-Difluoro-17-(p-fluorophenyl)-18,19,20-trinor-13-cis-
2,2-Difluoro-16-(methyl-17-phenyl-18,19,20-trinor-13-cis-
2,2-Difluoro-16,16-dimethyl-17-phenyl-18,19,20-trinor-13-cis-;
2,2,16-Trifluoro-17-phenyl-18,19,20-trinor-13-cis-;
2,2,16,16-Tetrafluoro-17-phenyl-18,19,20-trinor-13-cis-;
2,2-Difluoro-16-phenyl-17,18,19,20-tetranor-13-cis-;
2,2-Difluoro-16-(m-trifluoromethylphenyl)-17,18,19,20-tetranor-13-cis-;
2,2-Difluoro-16-(m-chlorophenyl)-17,18,19,20-tetranor-13-cis-;
2,2-Difluoro-16-(p-fluorophenyl)-17,18,19,20-tetranor-13-cis-;
2,2-Difluoro-16-phenyl-18,19,20-trinor-13-cis-;
2,2-Difluoro-16-methyl-16-phenyl-18,19,20-trinor-13-cis-;
2,2-Difluoro-16-phenoxy-17,18,19,20-tetranor-13-cis-;
2,2-Difluoro-16-(m-trifluoromethylphenoxy)-17,18,19,20-tetranor-13-cis-;

2,2-Difluoro-16-(m-chlorophenoxy)-17,18,19,20-tetranor-13-cis-;
2,2-Difluoro-16-(p-fluorophenoxy)-17,18,19,20-tetranor-13-cis-;
2,2-Difluoro-16-phenoxy-18,19,20-trinor-13-cis-;
2,2-Difluoro-16-methyl-16-phenoxy-18,19,20-trinor-13-cis-;
trans-2,3-Didehydro-;
trans-2,3-Didehydro-15-methyl-;
trans-2,3-Didehydro-16-methyl-;
trans-2,3-Didehydro-16,16-dimethyl-;
trans-2,3-Didehydro-16-fluoro-;
trans-2,3-Didehydro-16,16-difluoro-;
trans-2,3-Didehydro-17-phenyl-18,19,20-trinor-;
trans-2,3-Didehydro-17-(m-trifluoromethylphenyl)-18,19,20-trinor-;
trans-2,3-Didehydro-17-(m-chlorophenyl)-18,19,20-trinor-;
trans-2,3-Didehydro-17-(p-fluorophenyl)-18,19,20-trinor-;
trans-2,3-Didehydro-16-methyl-17-phenyl-18,19,20-trinor-;
trans-2,3-Didehydro-16,16-dimethyl-17-phenyl-18,19,20-trinor-;
trans-2,3-Didehydro-16-fluoro-17-phenyl-18,19,20-trinor-;
trans-2,3-Didehydro-16,16-difluoro-17-phenyl-18,19,20-trinor-;
trans-2,3-Didehydro-16-phenyl-17,18,19,20-tetranor-;
trans-2,3-Didehydro-16-(m-trifluoromethylphenyl)-17,18,19,20-tetranor-;
trans-2,3-Didehydro-16-(m-chlorophenyl)-17,18,19,20-tetranor-;
trans-2,3-Didehydro-16-(p-fluorophenyl)-17,18,19,20-tetranor-;
trans-2,3-Didehydro-16-phenyl-18,19,20-trinor-;
trans-2,3-Didehydro-16-methyl-16-phenyl-18,19,20-trinor-;
trans-2,3-Didehydro-16-phenoxy-17,18,19,20-tetranor-;
trans-2,3-Didehydro-16-(m-trifluoromethylphenoxy)-17,18,19,20-tetranor-;
trans-2,3-Didehydro-16-(m-chlorophenoxy)-17,18,19,20-tetranor-;
trans-2,3-Didehydro-16-(p-fluorophenoxy)-17,18,19,20-tetranor-;
trans-2,3-Didehydro-16-phenoxy-18,19,20-trinor-;
trans-2,3-Didehydro-16-methyl-16-phenoxy-18,19,20-trinor-;
trans-2,3-Didehydro-13,14-didehydro-;
trans-2,3-Didehydro-16-methyl-13,14-didehydro-;
trans-2,3-Didehydro-16,16-dimethyl-13,14-didehydro-;
trans-2,3-Didehydro-16-fluoro-13,14-didehydro-;
trans-2,3-Didehydro-16,16-difluoro-13,14-didehydro-;
trans-2,3-Didehydro-17-phenyl-18,19,20-trinor-13,14-didehydro-;
trans-2,3-Didehydro-17-(m-trifluoromethylphenyl)-18,19,20-trinor-13,14-didehydro-;
trans-2,3-Didehydro-17-(m-chlorophenyl)-18,19,20-trinor-13,14-didehydro-;
trans-2,3-Didehydro-17-(p-fluorophenyl)-18,19,20-trinor-13,14-didehydro-;
trans-2,3-Didehydro-16-methyl-17-phenyl-18,19,20-trinor-13,14-didehydro-;
trans-2,3-Didehydro-16,16-dimethyl-17-phenyl-18,19,20-trinor-13,14-didehydro-;
trans-2,3-Didehydro-16-fluoro-17-phenyl-18,19,20-trinor-13,14-didehydro-;

trans-2,3-Didehydro-16,16-difluoro-17-phenyl-18,19,20-trinor-13,14-didehydro-;
trans-2,3-Didehydro-16-phenyl-17,18,19,20-tetranor-13,14-didehydro-;
trans-2,3-Didehydro-16-(m-trifluoromethylphenyl)-17,18,19,20-tetranor-13,14-didehydro-;
trans-2,3-Didehydro-16-(m-chlorophenyl)-17,18,19,20-tetranor-13,14-didehydro-;
trans-2,3-Didehydro-16-phenyl-18,19,20-trinor-13,14-didehydro-;
trans-2,3-Didehydro-16-methyl-16-phenyl-18,19,20-trinor-13,14-didehydro-;
trans-2,3-Didehydro-16-phenoxy-17,18,19,20-tetranor-13,14-didehydro-;
trans-2,3-Didehydro-16-(m-trifluoromethylphenoxy)-17,18,19,20-tetranor-13,14-didehydro-;
trans-2,3-Didehydro-16-(m-chlorophenoxy)-17,18,19,20-tetranor-13,14-didehydro-;
trans-2,3-Didehydro-16-phenoxy-18,19,20-trinor-13,14-didehydro-;
trans-2,3-Didehydro-16-methyl-16-phenoxy-18,19,20-trinor-13,14-didehydro-;
trans-2,3-Didehydro-13,14-dihydro-;
trans-2,3-Didehydro-16-methyl-13,14-dihydro-;
trans-2,3-Didehydro-16,16-dimethyl-13,14-dihydro-;
trans-2,3-Didehydro-16-fluoro-13,14-dihydro-;
trans-2,3-Didehydro-16,16-difluoro-13,14-dihydro-;
trans-2,3-Didehydro-17-phenyl-18,19,20-trinor-13,14-dihydro-;
trans-2,3-Didehydro-17-(m-trifluoromethylphenyl)-18,19,20-trinor-13,14-dihydro-;
trans-2,3-Didehydro-17-(m-chlorophenyl)-18,19,20-trinor 13,14-dihydro-;
trans-2,3-Didehydro-17-(p-fluorophenyl)-18,19,20-trinor 13,14-dihydro-;
trans-2,3-Didehydro-16-methyl-17-phenyl-18,19,20-trinor 13,14-dihydro-;
trans-2,3-Didehydro-16,16-dimethyl-17-phenyl-18,19,20-trinor-13,14-dihydro-;
trans-2,3-Didehydro-16-fluoro-17-phenyl-18,19,20-trinor-13,14-dihydro-;
trans-2,3-Didehydro-16,16-difluoro-17-phenyl-18,19,20-trinor-13,14-dihydro-;
trans-2,3-Didehydro-16-phenyl-17,18,19,20-tetranor-13,14-dihydro-;
trans-2,3-Didehydro-16-(m-trifluoromethylphenyl)-17,18-19,20-tetranor-13,14-dihydro-;
trans-2,3-Didehydro-16-(m-chlorophenyl)-17,18,19,20-tetranor-13,14-dihydro-;
trans-2,3-Didehydro-16-(p-fluorophenyl)-17,18,19,20-tetranor-13,14-dihydro-;
trans-2,3-Didehydro-16-phenyl-18,19,20-trinor-13,14-dihydro-;
trans-2,3-Didehydro-16-methyl-16-phenyl-18,19,20-trinor-13,14-dihydro-;
trans-2,3-Didehydro-16-phenoxy-17,18,19,20-tetranor-13,14-dihydro-;
trans-2,3-Didehydro-16-(m-trifluoromethylphenoxy)-17,18,19,20-tetranor-13,14-dihydro-;
trans-2,3-Didehydro-16-(m-chlorophenoxy)-17,18,19,20-tetranor-13,14-dihydro-;
trans-2,3-Didehydro-16-(p-fluorophenoxy)-17,18,19,20-tetranor-13,14-dihydro-;
trans-2,3-Didehydro-16-phenoxy-18,19,20-trinor-13,14-dihydro-;
trans-2,3-Didehydro-16-methyl-16-phenoxy-18,19,20-trinor-13,14-dihydro-;
trans-2,3-Didehydro-13-cis-;
trans-2,3-Didehydro-16-methyl-13-cis-;
trans-2,3-Didehydro-16,16-dimethyl-13-cis-;
trans-2,3-Didehydro-16-fluoro-13-cis-;
trans-2,3-Didehydro-16,16-difluoro-13-cis-;
trans-2,3-Didehydro-17-phenyl-18,19,20-trinor-13-cis-;
trans-2,3-Didehydro-17-(m-trifluoromethylphenyl)-18,19,20-trinor-13-cis-;
trans-2,3-Didehydro-17-(m-chlorophenyl)-18,19,20-trinor-13-cis-;
trans-2,3-Didehydro-17-(p-fluorophenyl)-18,19,20-trinor-13-cis-;
trans-2,3-Didehydro-16-methyl-17-phenyl-18,19,20-trinor-13-cis-;
trans-2,3-Didehydro-16,16-dimethyl-17-phenyl-18,19,20-trinor-13-cis-;
trans-2,3-Didehydro-16-fluoro-17-phenyl-18,19,20-trinor-13-cis-;
trans-2,3-Didehydro-16,16-difluoro-17-phenyl-18,19,20-trinor-13-cis-;
trans-2,3-Didehydro-16-phenyl-17,18,19,20-tetranor-13,-cis-;
trans-2,3-Didehydro-16-(m-trifluoromethylphenyl)-17,18,19,20-tetranor-13-cis-;
trans-2,3-Didehydro-16-(m-chlorophenyl)-17,18,19,20-tetranor-13-cis-;
trans-2,3-Didehydro-16-(p-fluorophenyl)-17,18,19,20-tetranor-13-cis-;
trans-2,3-Didehydro-16-phenyl-18,19,20-trinor-13-cis-;
trans-2,3-Didehydro-16-methyl-16-phenyl-18,19,20-trinor-13-cis-;
trans-2,3-Didehydro-16-phenoxy-17,18,19,20-tetranor-13-cis-;
trans-2,3-Didehydro-16-(m-trifluoromethylphenoxy)-17,18,19,20-tetranor-13-cis-;
trans-2,3-Didehydro-16-(m-chlorophenoxy)-17,18,19,20-tetranor-13-cis-;
trans-2,3-Didehydro-16-(p-fluorophenoxy)-17,18,19,20-tetranor-13-cis-;
trans-2,3-Didehydro-16-phenoxy-18,19,20-trinor-13-cis-;
trans-2,3-Didehydro-16-methyl-16-phenoxy-18,19,20-trinor-13-cis-;
and their corresponding 11-deoxy-$PGF_1$ and 11-deoxy-11-hydroxymethyl-$PGF_1$ analogs.

Further, following procedures described above there are prepared the pharmacologically acceptable salts of the above free acids by neutralization with base corresponding to the free acid to be prepared.

Finally, there are prepared primary amines, N-alkyl amines, secondary amines and N,N-dialkyl tertiary amines from the above amides as described in U.S. Pat. No. 4,028,350; 2-decarboxy-2-tetrazolyl products from corresponding 2-decarboxy-2-tetrazolyl-PG-type reactants prepared according to U.S. Pat. No. 3,953,466; or 2-decarboxy-2-hydroxymethyl-PG-type compounds prepared by reduction of corresponding acids and esters according to U.S. Pat. No. 4,028,419.

I claim:

1. A prostacyclin analog of the formula

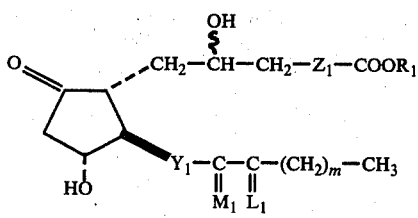

wherein $Z_1$ is
- (1) $-(CH_2)_g-CH_2-CH_2-$,
- (2) $-(CH_2)_g-CH_2-CF_2-$, or
- (3) trans-$(CH_2)_g-CH=CH-$, wherein g is the integer one, 2, or 3;
wherein $Y_1$ is
- (1) trans-$CH=CH-$,
- (2) cis-$CH=CH-$,
- (3) $-CH_2CH_2-$,
- (4) trans-$CH=C(Hal)-$, or
- (5) $-C\equiv C-$ wherein Hal is chloro or bromo;
wherein $M_1$ is

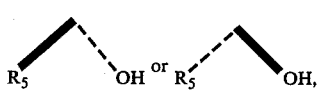

wherein $R_5$ is hydrogen or alkyl with one to 4 carbon atoms, inclusive;
wherein $L_1$ is

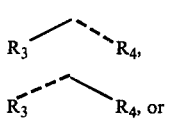

a mixture of

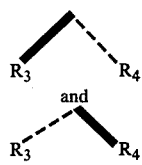

wherein $R_3$ and $R_4$ are hydrogen, methyl, or fluoro, being the same or different, with the proviso that one of $R_3$ and $R_4$ is fluoro only when the other is hydrogen or fluoro;

wherein $R_1$ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted with one, two, or three chloro or alkyl of one to 3 carbon atoms; phenyl substituted in the para position by

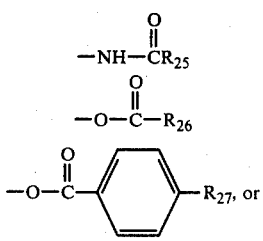

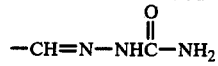

wherein $R_{25}$ is methyl, phenyl, acetamidophenyl, benzamidophenyl, or $-NH_2$; $R_{26}$ is methyl, phenyl, $-NH_2$, or methoxy; and $R_{27}$ is hydrogen or acetamido, inclusive; or a pharmacologically acceptable cation;
wherein m is the integer one to 5, inclusive.

2. A prostacyclin analog according to claim 1, wherein $\sim$OH is beta.

3. 6β-Hydroxy-PGE$_1$, a prostacyclin analog according to claim 2.

4. A prostacyclin analog according to claim 1, wherein $\sim$OH is alpha.

5. 6α-Hydroxy-PGE$_1$, a prostacyclin analog according to claim 4.

6. 6α-Hydroxy-15-methyl-PGE$_1$, a prostacyclin analog according to claim 4.

7. 6α-Hydroxy-16,16-dimethyl-PGE$_1$, a prostacyclin analog according to claim 4.

8. A prostacyclin analog according to claim 1, wherein $\sim$OH is a mixture of α-OH and β-OH.

9. A prostacyclin analog according to claim 8, wherein $Y_1$ is cis-$CH=CH-$.

10. 6-Hydroxy-cis-13-PGE$_1$, a prostacyclin analog according to claim 9.

11. A prostacyclin analog according to claim 8, wherein $Y_1$ is $-C\equiv C-$.

12. 6-Hydroxy-13,14-didehydro-PGE$_1$, a prostacyclin analog according to claim 11.

13. A prostacyclin analog according to claim 8, wherein $Y_1$ is trans-$CH=C(Hal)-$.

14. 6-Hydroxy-14-chloro-PGE$_1$, a prostacyclin analog according to claim 13.

15. A prostacyclin analog according to claim 8, wherein $Y_1$ is $-CH_2CH_2-$.

16. 6-Hydroxy-13,14-dihydro-PGE$_1$, a prostacyclin analog according to claim 15.

17. A prostacyclin analog according to claim 8, wherein $Y_1$ is trans-$CH=CH-$.

18. A prostacyclin analog according to claim 17, wherein $Z_1$ is $-(CH_2)_g-CH_2-CF_2-$.

19. 2,2-Difluoro-6-hydroxy-15-methyl-PGE$_1$, a prostacyclin analog according to claim 18.

20. A prostacyclin analog according to claim 17, wherein $Z_1$ is trans-$(CH_2)_g-CH=CH-$.

21. trans-2,3-Didehydro-6-hydroxy-PGE$_1$, a prostacyclin analog according to claim 20.

22. A prostacyclin analog according to claim 17, wherein $Z_1$ is $-(CH_2)_g-CH_2-CH_2-$.

23. A prostacyclin analog according to claim 22, wherein g is one.

24. A prostacyclin analog according to claim 23, wherein m is 3.

25. A prostacyclin analog according to claim 24, wherein $R_5$ is methyl.

26. 6-Hydroxy-15-methyl-PGE$_1$, a prostacyclin analog according to claim 25.

27. A prostacyclin analog according to claim 24, wherein $R_5$ is hydrogen.

28. A prostacyclin analog according to claim 27, wherein at least one of $R_3$ and $R_4$ is fluoro.

29. 6-Hydroxy-16,16-difluoro-PGE$_1$, a prostacyclin analog according to claim 28.

30. A prostacyclin analog according to claim 27, wherein at least one of $R_3$ and $R_4$ is methyl.

31. 6-Hydroxy-16,16-dimethyl-PGE$_1$, a prostacyclin analog according to claim 30.

32. A prostacyclin analog according to claim 27, wherein R$_3$ and R$_4$ are both hydrogen.

33. 6-Hydroxy-PGE$_1$, methyl ester, a prostacyclin analog according to claim 32.

34. 6-Hydroxy-PGE$_1$, tris(hydroxymethyl)aminomethane salt, a prostacyclin analog according to claim 32.

35. 6-Hydroxy-PGE$_1$, benzamidophenyl ester, a prostacyclin analog according to claim 32.

36. 6-Hydroxy-PGE$_1$, a prostacyclin analog according to claim 32.

* * * * *

UNITED STATES PATENT OFFICE
CERTIFICATE OF CORRECTION

Patent No. 4,131,738　　　　　　　　　　Dated 26 December 1978

Inventor(s) Herman W. Smith

It is certified that error appears in the above-identified patent and that said Letters Patent are hereby corrected as shown below:

Column 3, lines 15-22, that portion of the formula reading

Column 5, line 19, "$R_{21}$ and $R_{22}$ are" should read -- $R_{21}$ and $R_{23}$ are --; line 20, "-$NR_{22}R_{24}$," should read -- -$NR_{23}R_{24}$, --;

Column 6, line 36, "16-(substituted phenyl-18,19,20-trinor-" should read -- 16-(substituted phenyl)-18,19,20-trinor- --;

Column 7, line 20-21, "$R_3$ nor $R_3$ is methyl" should read -- $R_3$ nor $R_4$ is methyl --; line 31, "or 16-substituted phenoxy)-" should read -- or 16-(substituted phenoxy)- --;

Column 8, line 31, "(2,3,4-, 2,3,5-, 2,3,6-, or 2,4,5-trimethylphenyl," should read -- (2,3,4-, 2,3,5-, 2,3,6-, or 2,4,5-)trimethylphenyl, --;

Column 10, line 62-63, "$\alpha$-$\gamma$-dihydroxybutylamide," should read -- $\alpha$,$\delta$-dihydroxybutylamide, --;

Column 18, lines 57-67, that portion of formula XXVI reading

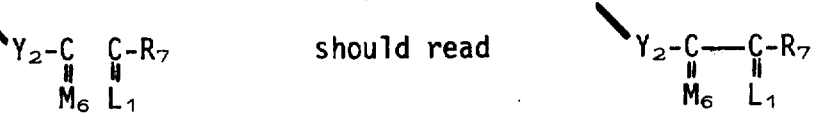

UNITED STATES PATENT OFFICE
CERTIFICATE OF CORRECTION

Patent No. 4,131,738       Dated 26 December 1978

Inventor(s) Herman W. Smith

It is certified that error appears in the above-identified patent and that said Letters Patent are hereby corrected as shown below:

Column 23, line 53, "-CH$_1$OSi(G$_1$)$_3$," should read -- -CH$_2$-OSi(G$_1$)$_3$, --;
Column 24, line 10, "ω-(tri-substituted silyl)oxy-alkyne," should read -- ω-(trisubstituted silyl)oxy-1-alkyne, --;
Column 37, line 11, "2,2-Trifluoro-" should read -- 2,2,16-Trifluoro- --; line 23, "2,2-Difluoro-16-phenyl-16-phenyl-" should read -- 2,2-Difluoro-16-phenyl- --.

Signed and Sealed this

Twenty-ninth Day of September 1981

[SEAL]

Attest:

Attesting Officer

GERALD J. MOSSINGHOFF

Commissioner of Patents and Trademarks